US011738061B2

(12) United States Patent
Doychinov et al.

(10) Patent No.: US 11,738,061 B2
(45) Date of Patent: Aug. 29, 2023

(54) NATURAL COMBINATION PRODUCTS AND METHODS FOR REGULATION OF KIDNEY AND EXCRETORY SYSTEM FUNCTION

(71) Applicant: Pure Care Pro LLC, Olympia, WA (US)

(72) Inventors: Plamen Doychinov Doychinov, Plovdiv (BG); Stoyan Doychinov Doychinov, Plovdiv (BG)

(73) Assignee: Pure Care Pro LLC, Olympia, WA (US)

( * ) Notice: Subject to any disclaimer, the term of this patent is extended or adjusted under 35 U.S.C. 154(b) by 0 days.

(21) Appl. No.: 16/978,595

(22) PCT Filed: Mar. 5, 2019

(86) PCT No.: PCT/US2019/020753
§ 371 (c)(1),
(2) Date: Sep. 4, 2020

(87) PCT Pub. No.: WO2019/173339
PCT Pub. Date: Sep. 12, 2019

(65) Prior Publication Data
US 2021/0060109 A1    Mar. 4, 2021

Related U.S. Application Data

(60) Provisional application No. 62/638,692, filed on Mar. 5, 2018.

(51) Int. Cl.
A61K 36/48        (2006.01)
A61P 13/12        (2006.01)
A61K 9/00         (2006.01)
A61K 9/28         (2006.01)
A61K 31/355       (2006.01)
A61K 31/4415      (2006.01)
A61K 33/26        (2006.01)
A61K 36/185       (2006.01)
A61K 36/45        (2006.01)
A61K 47/02        (2006.01)
A61K 47/12        (2006.01)
A61K 47/32        (2006.01)
A61K 47/38        (2006.01)

(52) U.S. Cl.
CPC ........... *A61K 36/48* (2013.01); *A61K 9/0053* (2013.01); *A61K 9/28* (2013.01); *A61K 31/355* (2013.01); *A61K 31/4415* (2013.01); *A61K 33/26* (2013.01); *A61K 36/185* (2013.01); *A61K 36/45* (2013.01); *A61K 47/02* (2013.01); *A61K 47/12* (2013.01); *A61K 47/32* (2013.01); *A61K 47/38* (2013.01); *A61P 13/12* (2018.01)

(58) Field of Classification Search
CPC ....... A61P 13/12; A61K 36/48; A61K 9/0053; A61K 9/28; A61K 31/355; A61K 31/4415; A61K 33/26; A61K 36/185; A61K 36/45; A61K 47/02; A61K 47/12; A61K 47/32; A61K 47/38
See application file for complete search history.

(56) References Cited

U.S. PATENT DOCUMENTS

| | | | | |
|---|---|---|---|---|
| 3,492,401 A | * | 1/1970 | Muhler | A61K 33/24 424/650 |
| 5,976,548 A | * | 11/1999 | Hsia | A23L 2/385 424/735 |
| 6,521,247 B1 | * | 2/2003 | deVries | A23L 33/15 424/439 |
| 8,257,694 B2 | * | 9/2012 | Daikeler | A61K 35/745 424/93.44 |
| 2009/0175969 A1 | * | 7/2009 | Krotkiewski | A61K 36/48 424/757 |
| 2010/0074969 A1 | | 3/2010 | Hughes et al. | |
| 2011/0288012 A1 | | 11/2011 | Somekawa et al. | |
| 2014/0141082 A1 | | 5/2014 | Gao | |

FOREIGN PATENT DOCUMENTS

| | | | | |
|---|---|---|---|---|
| BG | 66819 B1 | 1/2019 | | |
| GB | 1172408 | * 11/1969 | ............. | A61K 27/14 |

(Continued)

OTHER PUBLICATIONS

Laura Cornara, et al, Therapeutic Potential of Temperate Forage Legumes: A Review, 56 Crit. Rev. Food Sci. Nutr. S149 (Year: 2016).*
"Vitamin E (α-Tocopherol)," Micronutrient Information Center, Linus Pauling Institute, Oregon State University, Corvallis, OR, reviewed 2017, URL=https://lpi.oregonstate.edu/mic/vitamins/vitamin-E, accessed Jan. 19, 2021, 1 page.
Babitt et al., "Mechanisms of Anemia in CKD," *J. Am. Soc. Nephrol.* 23:1631-1634, 2012.
Benigni et al., "Inhibiting Angiotensin-Converting Enzyme Promotes Renal Repair by Limiting Progenitor Cell Proliferation and Restoring the Glomerular Architecture," *The American Journal of Pathology* 179(2):628-638, 2011.

(Continued)

*Primary Examiner* — Sean M Basquill
(74) *Attorney, Agent, or Firm* — Seed IP Law Group LLP

(57) ABSTRACT

This invention relates to compositions and methods relating to a combination of naturally-occurring active ingredients useful for the regulation of kidney and excretory system function. The combination of active ingredients, comprising vitamin $B_6$, vitamin E, iron, roundhead *Lespedeza*, birch leaf, and red bilberry, improves the function of kidney structures. The present invention may be used to achieve lower blood nitrogen content, including help to eliminate creatinine, urea, uric acid, by improving glomerular filtration and thus delaying hemodialysis. The present invention may be used to achieve a pronounced anti-inflammatory effect on the kidneys and the urinary tract. The present invention may also be used on its own or as a part of conventional treatment for a long time or indefinitely.

13 Claims, 7 Drawing Sheets

(56) References Cited

FOREIGN PATENT DOCUMENTS

| WO | 00/54784 A1 | 9/2000 |
|----|-------------|--------|
| WO | 01/12163 A1 | 2/2001 |

OTHER PUBLICATIONS

Besarab et al., "Iron supplementation to treat anemia in patients with chronic kidney disease," *Nat. Rev. Nephrol.* 6:699-710, 2010.

Campean et al., "Atherosclerosis and Vascular Calcification in Chronic Renal Failure," *Kidney Blood Press Res* 28:280-289, 2005.

Chen et al., "High homocysteine, low vitamin B-6, and increased oxidative stress are independently associated with the risk of chronic kidney disease," *Nutrition* 32:236-241, 2016.

Hänsel et al., *Pharmakognosie—Phytopharmazie*, Springer: Berlin, Heidelberg, Germany, 2010. (abstract only).

He et al., "Cranberry Phytochemicals: Isolation, Structure Elucidation, and Their Antiproliferative and Antioxidant Activities," *J. Agric. Food Chem.* 54:7069-7074, 2006.

Karonen et al., "Quantitative analysis of polymeric proanthocyanidins in birch leaves with normal-phase HPLC," *Phytochem. Anal.* 17:149-156, 2006.

Kobuchi et al., "Quercetin inhibits inducible ICAM-1 expression in human endothelial cells through the JNK pathway," *Am. J. Physiol.* 277:C403-411, 1999.

Lahtinen et al., "HPLC Analysis of Leaf Surface Flavonoids for the Preliminary Classification of Birch Species," *Phytochem. Anal.* 17:197-203, 2006.

Liu et al., "Role of Cranberry Juice on Molecular-Scale Surface Characteristics and Adhesion Behavior of *Escherichia coli*," *Biotechnol. Bioeng.* 93(2):297-305, 2006, (9 pages).

Locatelli et al., "Iron Therapy Challenges for the Treatment of Nondialysis CKD Patients," *Clin. J. Am. Soc. Nephrol.* 11:1269-1280, 2016.

Lowe et al., "Cranberry juice and urinary tract infections: what is the evidence?" *Urology* 57:407-413, 2001.

Mydlik et al., "Metabolic Disorders of Vitamin $B_6$ in Chronic Kidney Disease Patients," *BANTAO J.* 7(2):33-36, 2009.

Ossipov et al., "High-performance liquid chromatographic separation and identification of phenolic compounds from leaves of *Betula puhescens* and *Betula pendula*," *J. Chromatogr. A* 721(1):59-68, 1996.

Pappas et al., "Phytochemicals of Cranberries and Cranberry Products: Characterization, Potential Health Effects, and Processing Stability," *Crit. Rev. in Food Sci. Nutri.* 49:741-781, 2009.

Scalbert, "Antimicrobial properties of tannins," *Phytochemistry* 30(12):3875-3883, 1991.

Small et al., "Oxidative Stress and Antioxidant Therapy in Chronic Kidney and Cardiovascular Disease," *Nephrology* 17(4):233-264, 2012.

Sobota, "Inhibition of bacterial adherence by cranberry juice: potential use for the treatment of urinary tract infections," *J. Urol.* 131(5):1013-1016, 1984.

The National Kidney Foundation, "Understanding Your Lab Values," reviewed Feb. 2, 2017, URL=https://www.kidney.org/atoz/content/understanding-you-lab-values, accessed Apr. 24, 2019, 3 pages.

Tsai et al., "Serum Uric Acid and Progression of Kidney Disease: A Longitudinal Analysis and Mini-Review," *PLoS ONE* 12(1):e0170393, 2017. (16 pages).

Wang et al., "A New Monoterpene Glucoside from the Leaves of *Betula platyphylla* Suk," *Chin. Chem. Letters* 12(4):343-344, 2001.

Yarnell, "Botanical medicines for the urinary tract," *World J. Urol.* 20:285-293, 2002.

Young et al., "Asymmetric Dimethylarginine and Mortality in Stages 3 to 4 Chronic Kidney Disease," *Clin. J. Am. Soc. Nephrol.* 4:1115-1120, 2009.

Zlatkov et al., "Use of Renohelp M in patients with recurrent urinary tract infections," *Meditsinski Pregled / Medical Review* 50(2):35-39, 2014, (abstract only).

\* cited by examiner

NATURAL COMBINATION PRODUCTS AND METHODS FOR REGULATION OF KIDNEY AND EXCRETORY SYSTEM FUNCTION

BACKGROUND

Technical Field

This invention relates to compositions and methods relating to a combination comprising naturally-occurring active ingredients useful for the regulation of kidney and excretory system function. The inventive combination of active ingredients, including vitamin $B_6$, vitamin E, iron, roundhead *Lespedeza*, birch leaf, and red bilberry, improve the function of kidney structures. The present invention may be used to achieve lower blood nitrogen content, including help to eliminate creatinine, urea, uric acid, by improving glomerular filtration; thus, delaying hemodialysis. The present invention may be used to achieve a pronounced anti-inflammatory effect on the kidneys and the urinary tract. The present invention may also be used on its own or as a part of conventional treatment for a long time or indefinitely. The present invention comprises singular compositions and formulations that may provide a synergistic, multi-faceted approach to addressing diseases and conditions associated with disorders of kidney function and the excretory system. Further, the present invention may achieve new and beneficial efficiencies and avenues of recourse to better respond to complications that accompany, for example, chronic kidney disease (CKD).

Description of the Related Art

There are several diseases and conditions associated with disorders of kidney function and the excretory system. Such diseases and conditions include, but are not limited to: acute and chronic pyelonephritis, chronic glomerulonephritis, metabolic diseases (e.g., dilated nephropathy, diabetic nephropathy, kidney amyloidosis), chronic kidney damage in kidney stone disease, chronic kidney damage in systemic connective tissue diseases (e.g., lupus nephropathy, polyarteritis *nodosa*), tubulointerstitial nephritis (e.g., analgesic nephropathy, Balkan endemic nephropathy), kidney polycystic disease, renal impairment during and after chemotherapy, and acute and chronic cystitis.

The kidneys, as the primary functional organ of the excretory system, play a key role in eliminating the waste products from protein metabolism, participate in the maintenance of the alkaline-acid balance in the body, have hormonal activity associated with maintaining blood pressure and hematopoiesis, and with regulating calcium-phosphorus metabolism.

The primary cleansing function of the kidneys is related to the homeostasis of body fluid compositions in terms of volume, pH, osmolarity and ionic concentrations. Kidneys are also responsible for the release of metabolic products (urea, creatinine, uric acid, etc.) and, together with the liver, the release of chemical compounds foreign to the organism. The kidneys also have incretory functions involved in important systems through the renin-angiotensin system, vitamin D3, and erythropoietin.

The nephron is a basic structural and functional unit of the kidneys. Each nephron contains a filtration unit known as a renal corpuscle, made up of a glomerulus and a Schumlansky-Bowman capsule, in which blood plasma is filtered.

There is a trend towards a progressive increase in kidney diseases worldwide. This is associated, on the one hand, with the uncontrolled and random intake of various medications (self-medication) and, on the other, with an increase in the number of patients with arterial hypertension and diabetes mellitus.

Various major diseases and metabolic disorders in the body lead to progressive impairment of renal function. Without adequate treatment, failure of essential kidney functions occurs leading to chronic kidney disease (CKD) with different degrees of severity. With irreversible loss of renal functions, chronic kidney failure (CKF) occurs.

The goal of patient treatment for patients suffering acute or chronic kidney disease or chronic kidney failure (CKF) of stages I, II and III is to prevent the progression of disease and to postpone the need for hemodialysis treatment. For such patients the present invention, alone or as part of the conventional treatment, may be beneficially used.

Urinary infections rank second in incidence rate among inflammatory diseases in humans after those of the lungs. Urinary infections are non-specific, destructive diseases of the renal interstitium, renal pelvis, and urinary tracts that occur mostly due to direct infection of bacteria, more rarely viruses or mycoplasmas, accompanied by an inflammatory response by the patient. Some common causative infection agents are: Gram-negative bacteria (*Escherichia coli, Klebsiella, Proteus, Pseudomonas, Acinetobacter, Serratia*), Gram-positive bacteria (Enterococci, Staphylococci, Chlamydiae—*Chlamydia trachomatis*), more rarely fungi (e.g., *Candida albicans*), *trichomonas*, gonococci, viruses, and the tuberculosis agent. Most often, urological infections recur in diabetics, patients with suppressed immune systems, and patients with high comorbidity, fatigue, and stress. The present invention may demonstrate antibacterial properties in inflammatory urinary tract infections such as these.

There exists a need for products and methods to help achieve regulation of kidney and excretory system function. More specifically, there is a need for compositions that are easy to use and administer, and singular compositions that provide a multi-faceted approach to addressing diseases and conditions associated with disorders of kidney function and the excretory system.

BRIEF SUMMARY

The present inventive combination of active ingredients, comprising vitamin $B_6$, vitamin E, iron, roundhead *Lespedeza*, birch leaf, and red bilberry, provide singular compositions that provide a multi-faceted approach to addressing diseases and conditions associated with disorders of kidney function and the excretory system. Compositions of the present invention may be used by subjects in need thereof to improve the function of kidney structures or overall general health. The present invention may be used to achieve lower blood nitrogen content, including by helping to eliminate creatinine, urea, and uric acid, by improving glomerular filtration. Thus, the present invention provides compositions and methods for subjects in need thereof that may be used to effectively delay hemodialysis. The present invention may be used to achieve a pronounced anti-inflammatory effect on the kidneys and the urinary tract. The present invention may also be used on its own or as a part of conventional treatment. The present invention may be used for a limited period of time (one or more days or weeks or one, two, three, four, five, six, seven, eight, nine, ten, or eleven months), a long time (one or more years), or indefinitely.

This invention provides improved compositions and methods for regulation of kidney and excretory system function for subjects in need thereof. The present invention may provide to subjects in need thereof one or more of the following benefits: positive cleansing action of nitrogen-containing products; improvement of kidney excretory function, which is demonstrated by an increase in creatinine clearance; anti-gout action by lowering uric acid; diuretic effect by increasing glomerular filtration; reducing blood pressure through increased diuresis; and possible inhibition of angiotensin converting enzyme (ACE).

The present invention achieves the many benefits noted herein by providing a unique combination of vitamin $B_6$, vitamin E, iron, roundhead *Lespedeza*, birch leaf, and red bilberry. In a specific embodiment, the present invention includes products comprising vitamin $B_6$, vitamin E, iron, roundhead *Lespedeza*, birch leaf, and red bilberry and methods of using the products for regulation of kidney and excretory system function for subjects in need thereof. The active agents of the present inventive compositions are particularly well-suited for addressing regulation of kidney functions relating to diseases and conditions associated with disorders of kidney function and the excretory system, including addressing complications that accompany development of CKD.

It is contemplated by the inventors that the herbal components, preferably in the form of extracts, of the compositions described herein may have a mutually potentiating effect or synergistic effect on each other. Further, the inventors contemplate that the vitamin $B_6$, vitamin E, and iron in the present compositions have a beneficial effect on the complications accompanying CKD. Additionally, the active agents, i.e., the vitamin $B_6$, vitamin E, iron, roundhead *Lespedeza*, birch leaf, and red bilberry, may have a potentiating synergistic effect when provided in the inventive combinations described herein. Further, it is understood by the inventors that all of the ingredients together, upon combination, may achieve a synergistic, significant and broad-spectrum effect.

The inventive compositions and methods for modifying, controlling, or regulating kidney and excretory system function may comprise a composition that includes the following ratio by weight (w/w) of active components:
vitamin $B_6$ from 0.005% to 3%;
vitamin E from 0.005% to 8%;
iron from 0.005% to 6%;
roundhead *Lespedeza* extract from 30% to 60%;
birch leaf extract from 30% to 60%; and
red bilberry extract from 5% to 30%.

The red bilberry extract referred to herein includes, but is not limited to, *Vaccinium hirtum* Thunb. extract.

In a preferred formulation, a dosage form is provided that includes, per capsule or tablet, about 649 mg of active components as follows: about 4 mg vitamin $B_6$ (pyridoxine HCL), about 9 mg vitamin E (natural d-α-tocopherol; about 10 IU), about 6 mg iron (as ferrous gluconate), about 280 mg dry extract of roundhead *Lespedeza* (stem and leaf, or aerial part of the plant, comprising lespedine and lespecapitoside), about 250 mg dry extract of birch leaf (leaf), and about 100 mg dry extract of red bilberry (*Vaccinium hirtum* Thunb.) extract (fruit). Thus, in this preferred formulation, the ratio by weight (w/w) of active components is about 0.6% vitamin $B_6$, about 1.4% vitamin E, about 0.9% iron, about 43% dry extract of roundhead *Lespedeza*, about 39% dry extract of birch leaf, and about 15% dry extract of red bilberry.

In one alternative formulation, a dosage form is provided that includes, per capsule or tablet, about 619 mg of active components as follows: about 4 mg vitamin $B_6$ (pyridoxine HCl), about 9 mg vitamin E (natural d-α-tocopherol; 10 IU), about 6 mg iron (as ferrous gluconate), about 250 mg dry extract of roundhead *Lespedeza* (stem and leaf, or aerial part of the plant, comprising lespedine and lespecapitoside), about 250 mg dry extract of birch leaf (leaf), and about 100 mg dry extract of red bilberry (*Vaccinium hirtum* Thunb.) (fruit). Thus, in this alternative formulation, the ratio by weight (w/w) of active components is about 0.6% vitamin $B_6$, about 1.5% vitamin E, about 1% iron, about 40% dry extract of roundhead *Lespedeza*, about 40% dry extract of birch leaf, and about 16% dry extract of red bilberry.

Additional ingredients, or excipients, may include but are not limited to, for example, microcrystalline cellulose, polyvinylpyrrolidone, talc, magnesium stearate, and film coating. For example, microcrystalline cellulose may be added in an amount of about 151 mg, polyvinylpyrrolidone may be added in an amount of about 35 mg, magnesium stearate may be added in an amount of about 5 mg, talc may be added in an amount of about 10 mg, and film coating may be added in an amount of about 30 mg (e.g., for tablet formulations).

In one embodiment of the formulation noted above, the dosage form comprises or consists of about 619 mg of active components and may comprise an additional about 231 mg of excipients, for a total dosage form weight of about 850 mg. Thus, in this formulation, the ratio by weight (w/w) of total dosage form weight for the active agents is about 0.5% vitamin $B_6$, about 1.1% vitamin E, about 0.7% iron, about 29% dry extract of roundhead *Lespedeza*, about 29% dry extract of birch leaf, and about 12% dry extract of red bilberry, with the remaining about 231 mg of excipients comprising about 27% or about one-fourth to about one-third of the total dosage form weight.

In another embodiment of the formulation noted above, the dosage form comprises or consist of about 649 mg of active components and may comprise an additional about 201 mg of excipients; for example microcrystalline cellulose may be added in an amount of about 121 mg, polyvinylpyrrolidone may be added in an amount of about 35 mg, magnesium stearate may be added in an amount of about 5 mg, talc may be added in an amount of about 10 mg, and film coating may be added in an amount of about 30 mg (e.g., for tablet formulations), for a total dosage form weight of about 850 mg. Thus, in this formulation, the ratio by weight (w/w) of total dosage form weight for the active agents is about 0.5% vitamin $B_6$, about 1.1% vitamin E, about 0.7% iron, about 34% dry extract of roundhead *Lespedeza*, about 29% dry extract of birch leaf, and about 12% dry extract of red bilberry, with the remaining about 201 mg of excipients comprising about 24% or about one-fifth to about one-third of the total dosage form weight.

Products of the present invention may comprise different dosage forms including, for example, tablets, capsules, powders, liquid, etc. Many other excipients known to those skilled in the art may be used depending of the different dosage forms to be used (e.g., capsules, powders, liquid).

Here, a preferred embodiment relates to capsules, because capsule formulations comprise minimal additional ingredients while providing moisture resistance and overcoming unpleasant tastes and odors. Capsule formulations are also easy to swallow and may leave no trace of the capsule contents in the throat and trachea. The capsule may contain, for example, hydroxypropyl methylcellulose (also known as HPMC or hypromellose), pullulan, gelatin, starch from cassava root or other vegetable sources, or cellulose.

An alternative embodiment relates to tablets, and preferably film-coated tablets, because coating provides moisture protection and helps to overcome unpleasant tastes and odors. The tablets are made to be swallowed very easily and to leave no trace in the throat and trachea.

The following Table 1 provides a listing of active substances, relative content in measurements of weight (w/w) per dosage form and proposed total content of two proposed daily intake regimens. It is noted that, while formulations may vary, a preferred embodiment of the present invention, showing active agents only, is presented in the table below.

TABLE 1

| Active Agent Name | Per 1 (one) tablet | Daily (3 tablets) |
| --- | --- | --- |
| Formulation 1: | | |
| Vitamin $B_6$ (pyridoxine HCl) | 4 mg | 12 mg |
| Vitamin E (natural d-α-tocopherol) | 10 IU (9 mg) | 30 IU (27 mg) |
| Iron (as ferrous gluconate) | 6 mg | 18 mg |
| Round-Head Lespedeza Dry Extract (stem and leaf) Lespedine Lespecapitoside | 280 mg | 840 mg |
| Birch Leaf Dry Extract (leaf) | 250 mg | 750 mg |
| Red Bilberry (*Vaccinium hirtum* Thunb.) Dry Extract (fruit) | 100 mg | 300 mg |
| Total: | 649 mg | 1947 mg |
| Formulation 2: | | |
| Vitamin $B_6$ (pyridoxine HCl) | 4 mg | 12 mg |
| Vitamin E (natural d-α-tocopherol) | 10 IU (9 mg) | 30 IU (27 mg) |
| Iron (as ferrous gluconate) | 6 mg | 18 mg |
| Round-Head Lespedeza Dry Extract (stem and leaf) Lespedine Lespecapitoside | 250 mg | 750 mg |
| Birch Leaf Dry Extract (leaf) | 250 mg | 750 mg |
| Red Bilberry (*Vaccinium hirtum* Thunb.) Dry Extract (fruit) | 100 mg | 300 mg |
| Total: | 619 mg | 1857 mg |

It is contemplated that formulations permitting some deviation in the amounts, or relative amounts, of the six active ingredients noted above may also serve the objectives of the present invention. Nonetheless, formulations providing variation from the stated amounts of active agent ratios that are still within about 5% (w/w) to about 10% (w/w) of the stated amounts of the total active agent weight (as opposed to the total composition weight including any excipients or additional ingredients) are most preferred. That is, potential formulation variations of active agent ratios may include, for example, vitamin $B_6$ in amounts ranging from about 3.5-4.5 mg (w/w), vitamin E in amounts ranging from about 8-10 mg (w/w), iron in amounts ranging from about 5.5-6.5 mg (w/w), dry extract of roundhead *Lespedeza* in amounts ranging from about 225-310 mg (w/w), dry extract of birch leaf in amounts ranging from about 225-275 mg (w/w), and dry extract of red bilberry in amounts ranging from about 90-110 mg (w/w).

Each of vitamin $B_6$, vitamin E, iron, roundhead *Lespedeza*, birch leaf, and red bilberry has been separately shown to affect the function of kidney structures. The present invention provides, for the first time, the combination of these six active components that, in turn, may work synergistically to trigger different mechanisms of action to affect regulation of kidney and excretory system function.

Each component individually has an effect on regulation of kidney and excretory system function but together they affect several different changes to the metabolic pathways contributing to dysregulation of kidney and excretory system function. Accordingly, the present invention, by combination, significantly increases the effectiveness of each of the active agents provided in the compositions of the present invention. The herbal extract ingredients, i.e., the roundhead *Lespedeza*, birch leaf, and red bilberry, may have a mutually potentiating effect (synergistic) on each other and the other components of the composition or formulation. Meanwhile, the vitamin $B_6$, vitamin E, and iron may produce an enhanced effect with regard to addressing the complications accompanying CKD. All the active ingredients, considered together or in combination, may have a synergistic, significant, and broad-spectrum effect. That is, each ingredient may have a potentiating synergistic effect when used as part of this inventive combination.

Vitamin $B_6$, in the form of pyridoxine HCl, may be the Vitamin $B_6$ active agent of the present invention. Vitamin $B_6$ exists in vivo as six compounds. These are pyridoxal, pyridoxine, pyridoxamine, and the 5' phosphates of these three compounds.

Vitamin E (α-tocopherol) is a naturally-occurring form of vitamin E, a fat-soluble vitamin with potent antioxidant properties.

Iron, in the form of ferrous gluconate, may be the iron active agent of the present invention. Iron deficiency is prevalent in patients with CKD, and use of oral and intravenous iron in patients with CKD who do not require dialysis might obviate or delay the need for treatment with erythropoiesis-stimulating agents (ESAs).

Roundhead *Lespedeza*, in the form of round head *Lespedeza* extract (stem and leaf, or aerial part of the plant) comprising lespedine and lespecapitoside, may be the roundhead *Lespedeza* iron active agent of the present invention. *Lespedeza capitata* is a perennial plant belonging to the Fabaceae family (legumes), spread throughout North America, China, Japan, and India. *Lespedeza* is in the form of different species, including *capitata*. The active functional part of *Lespedeza capitata* are flavonoids, including lespedine (kampferitrin), lespecapitoside, calein and others that are important for glomerular filtration and have a significant effect on renal activity. Roundhead *Lespedeza* extract may be made using the above-ground portions of the plant, including stems and leaves. The extract may be in the form of a liquid or it may be in a dry form, such as a powder.

Birch leaves contain 1-3% flavonol glycosides, mainly hyperoside and others, quercetin (3,5,7,3',4'-penta-hydroxyl-flavone) glycosides, kempferol (7-tetra-hydroxyl-flavone) glycosides, and myricetin. Birch leaf extract may be in the form of a liquid or it may be in a dry form, such as a powder. Birch leaf extract may be an active agent of the present invention.

Red bilberry, a member of the *Vaccinium* genus closely related to cranberries, has been used as a medicine for centuries and red bilberry extract may be an active agent of the present invention. Today cranberry is known for its numerous health effects. Of particular importance is the ability of cranberry to prevent urinary tract infections due to its unique antibacterial effect. Berries are rich in vitamins, trace elements, minerals, tannins, flavonoids, essential fatty acids—linoleic acid (omega 6), alphalinoleic acid (omega 3), carotenoids, and phytosterols. They contain about 6% of arbutein, traces of hydroquinone, about 8% of catechinic tannins, flavonoids like quercetin, hyperoside, isoquercetin, ursolic and chlorogenic acids, and vitamins C, A, and E. Red bilberry extract may be may be made using the fruit of the red bilberry plant, *Vaccinium hirtum* Thunb. The extract may be in the form of a liquid or it may be in a dry form, such as a powder.

These six main ingredients increase the effectiveness of compositions of the present invention due to the combination of their respective activities. It is also believed that the combination of these ingredients may produce a synergistic effect to facilitate regulation of kidney and excretory system function for subjects in need thereof.

The present invention comprises naturally sourced active agents for use in the composition that may reduce the risk of side effects as compared to non-naturally derived medicines. The present invention may also ensure long-lasting safety, allowing the compositions and methods disclosed herein to be included in different treatment regimens. The simultaneous action of the six active agent components on multiple distinct aspects of regulation of kidney and excretory system function results in significantly increased product efficacy compared to the effects imparted by each of the active agents alone. That is, the effects of each of the active agents in the compositions are not merely additive, but may be synergistic, when combined in accordance with the present invention.

DETAILED DESCRIPTION

Figure 1:
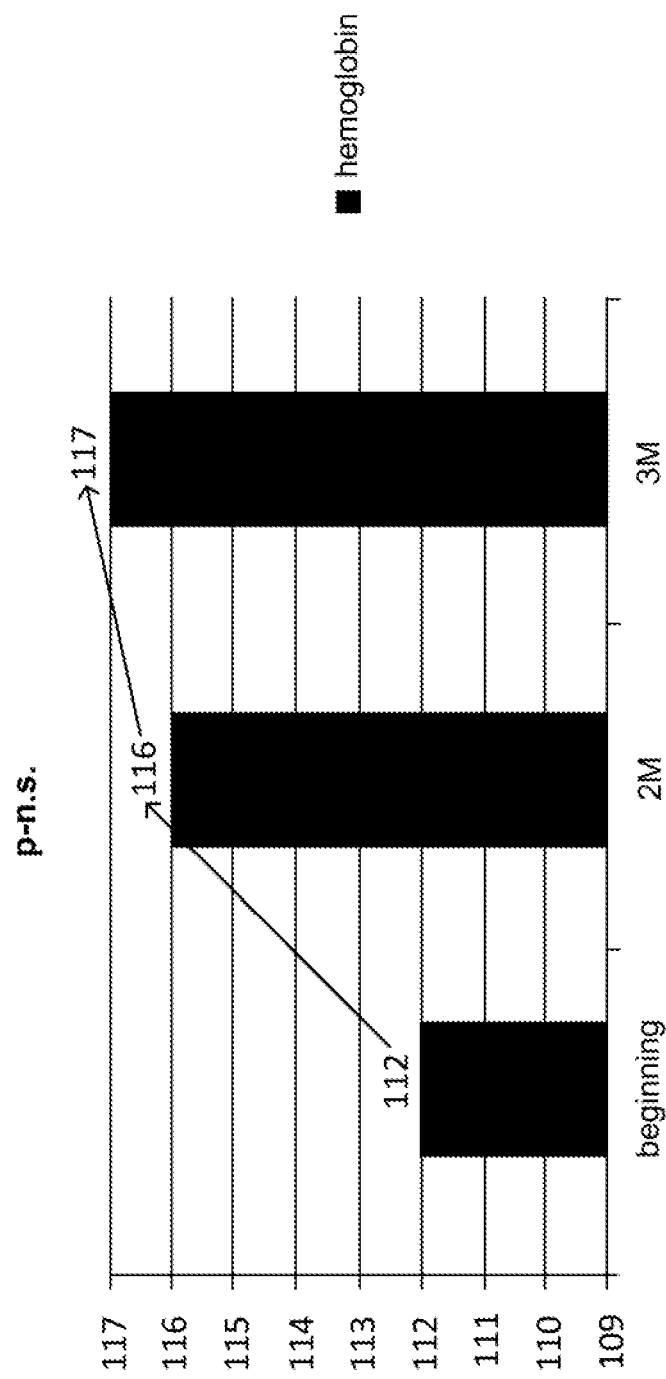
FIG. 1 illustrates the average hemoglobin level of the study patients measured at the beginning of the study, after 60 days ("2M"), and at the end of the study after 90 days ("3M"), shown in g/l.

The present invention includes products and methods of using products comprising natural ingredients, such as of vitamin $B_6$, vitamin E, iron, roundhead *Lespedeza*, birch leaf, and red bilberry, to form compositions useful for the regulation of kidney and excretory system function.

Active Agents

1. Vitamin $B_6$

Vitamin $B_6$ exists in vivo as six compounds. These are pyridoxal, pyridoxine, pyridoxamine, and the 5' phosphates of these three compounds. Vitamin $B_6$ is a water-soluble vitamin which is important for the normal function of multiple organ systems. It is metabolized to the active molecule pyridoxal-5-phosphate (PLP), which serves as the coenzyme for more than 100 enzymes. PLP influences protein and lipid metabolism, metabolism of several amino acids and formation of antibodies. Vitamin $B_6$ also catalyzes transformation of glyoxalate to glycine, which is part of the salvage metabolism mechanism preventing oxalate formation. Causes of vitamin $B_6$ deficiency in chronic kidney diseases patients include: decreased amount in diet, altered phosphorylation of pyridoxal on PLP, increased degradation of PLP or absorption in tissues, and vitamin $B_6$ loss through dialysis membranes. (Mydlik et al., *Metabolic Disorders of Vitamin B6 in Chronic Kidney Disease Patients*, $IV^{th}$ Internal Clinic, Faculty Hospital of L. Pasteur, Institute of Experimental Medicine, Medical School of P. J. Safarik University, Kosice, Slovak Republic (2009)).

High homocysteine, low pyridoxal-5-phosphate (PLP), increased oxidative stress, and decreased antioxidant enzyme activity (superoxide dismutase activity) may be independent contributing factors in the development of CKD.

Hyperhomocysteinemia is often seen in patients with CKD and is associated with the later development of vascular disease in patients with CKD. In homocysteine metabolism, methyl tetrahydrofolate is an essential co-substrate for homocysteine re-methylation to methionine. When there is an excess of methionine, homocysteine is directed to the transsulfuration pathway. In the transsulfuration of homocysteine metabolism, homocysteine is converted to cystathionine and then to cysteine by enzymes dependent on pyridoxal 50-phosphate (PLP, the physiological coenzyme form of vitamin $B_6$). Studies have reported that low folate and vitamin $B_6$ were significantly associated with high homocysteine concentrations in patients with CKD and end-stage renal disease. However, whether folate and vitamin $B_6$ are independently related to the risk of CKD or mediate the risk of CKD in connection with high homocysteine levels is unknown.

Excessive free radicals might gradually overload and exhaust the antioxidant defense system during the progression of CKD. Therefore, increased oxidative stress and decreased antioxidant capacities have been found to be associated with the risk of CKD.

Elevated plasma homocysteine and reduced folate or PLP concentrations may induce excessive production of reactive oxygen species, thus leading to greater oxidative stress and decreased antioxidant enzyme activities. It would be reasonable to hypothesize that higher homocysteine and lower folate or PLP would affect oxidative stress and, as a consequence, the entire antioxidant defense system, possibly triggering the development of CKD.

However, the associations of homocysteine, folate, and PLP with oxidative stress and antioxidant capacities in patients with CKD are still not entirely clear. (Chen et al, High homocysteine, low vitamin B-6, and increased oxidative stress are independently associated with the risk of chronic kidney disease, Nutrition 2016 February; 32(2):236-41).

Vitamin $B_6$ as used in the present invention may be sourced from conventional and commercially available resources.

2. Vitamin E

Vitamin E, such as α-tocopherol, is a naturally-occurring fat-soluble vitamin with potent antioxidant properties. Fats, which are an integral part of all cell membranes, are vulnerable to damage through lipid peroxidation by free radicals. Vitamin E, such as α-tocopherol, is uniquely suited to intercept peroxyl radicals and thus prevent a chain reaction of lipid oxidation. When a molecule of α-tocopherol neutralizes a free radical, it is oxidized and its antioxidant capacity is lost. Other antioxidants, such as vitamin C, are capable of regenerating the antioxidant capacity of α-tocopherol. (Micronutrient Information Center, Linus Pauling Institute, Oregon State University, Corvallis, Oreg. May 2015. Retrieved 7 Mar. 2017; website available at: lpi.oregonstate.edu/mic/vitamins/vitamin-E.)

Administration of α-tocopherol to kidney proximal tubular cells in culture decreased cisplatin-induced reactive oxygen species (ROS) and increased cell viability. The beneficial effects of α-tocopherol are not limited to its antioxidant properties, and recently attention has focused on its blood oxygenizing and endogenous cell signaling functions. (Small et al., Oxidative *Stress and Antioxidant Therapy in Chronic Kidney and Cardiovascular Disease*, NEPHROLOGY, 2012 May; 17(4):311-21).

Endothelium-derived nitric oxide, an important mediator of vascular tone and blood pressure regulation, is produced via reaction catalyzed by nitric oxide synthase. Asymmetric dimethylarginine (ADMA), a byproduct of the breakdown of arginine methylated proteins, is an endogenous inhibitor of this reaction. Increased ADMA levels lead to nitric oxide depletion, impaired endothelium-dependent vasodilation, reduced free radical scavenging, and plaque rupture with thrombus formation. Plasma concentrations of ADMA are elevated in cardiovascular high-risk states such as hypertension, obesity, and diabetes and seem to be related to endothelial dysfunction in patients with these conditions. High ADMA levels are an index of carotid intima-media thickness and are associated with future acute coronary events in general population studies. Levels of ADMA are elevated in chronic kidney disease (CKD). This 202-Da amino acid is eliminated unchanged in the urine but is also taken up and degraded in the kidney by the enzyme dimethylarginine dimethylaminohydrolase (DDAH). ADMA accumulation in kidney failure is due to both decreased elimination and reduced DDAH activity. High ADMA was an independent risk factor for cardiovascular disease (CVD) and all-cause mortality in a cohort of patients who were on hemodialysis and was associated with faster rates of kidney disease progression in patients in the earlier stages of CKD. However, data are limited on the relationship between ADMA levels and CVD in patients with CKD before reaching kidney failure. There are many studies that prove the relationship of ADMA with prevalent CVD and with all cause and CVD mortality during long-term follow-up of a cohort of patients with stages 3 to 4 CKD.

Some studies conducted in the United States show that administration of vitamin E results in reductions in ADMA levels without alterations in other circulating markers of oxidant stress in patients with CKD. (Young et al., *Asymmetric Dimethylarginine and Mortality in Stages* 3 *to* 4 *Chronic Kidney Disease*, CLIN. J. AM. SOC. NEPHROL. 4: 1115-1120 (2009)).

An important problem in patients with CDK is the extent of atherosclerosis, which is undoubtedly high in patients with chronic renal failure, and the consequences, i.e. cardiovascular events, represent a major clinical problem in these patients. Experimental findings now confirm an acceleration of atherosclerosis under the conditions of renal failure as well as early up-regulation of markers of inflammation and oxidative stress. The process apparently begins very early in the development of chronic renal failure and is accompanied by endothelial dysfunction and increased oxidative stress. The course of the disease is characterized by a more severe calcification of plaques and the arterial media. Increased knowledge about the pathogenesis of early and late atherosclerotic lesions in renal failure may open the possibility for prevention of lesion formation and adequate treatment thus representing further arguments for the early examination of kidney disease patients by a nephrologist. In addition to the well-described traditional risk factors, new uremic-specific, non-classic risk factors have been identified such as micro-inflammation, hyperphosphatemia and oxidative stress whose treatment includes potentially important clinical implications. (Campean et al., *Atherosclerosis and Vascular Calcification in Chronic Renal Failure*, KIDNEY BLOOD PRESS RES. 2005; 28(5-6):280-9).

Vitamin E as used in the present invention may be sourced from conventional and commercially available resources.

3. Iron

Iron, such as ferrous gluconate, may form part of this invention.

Iron deficiency is prevalent in patients with CKD, and use of oral and intravenous iron in patients with CKD who do not require dialysis might obviate or delay the need for treatment with erythropoiesis-stimulating agents (ESAs). Besarab et al., *Iron supplementation to treat anemia in patients with chronic kidney disease*, NAT. REV. NEPHROL. 2010 December; 6(12):699-710.

Anemia can happen early in the course of kidney disease and grow worse as kidneys fail and can no longer make erythropoietin (EPO). Anemia of CKD is a multifactorial process due to relative EPO deficiency, uremic-induced inhibitors of erythropoiesis, shortened erythrocyte survival, and disordered iron homeostasis. (Babitt et al., *Mechanisms of Anemia in CKD*, J. AM. SOC. NEPHROL. 2012 Sep. 28; 23(10): 1631-1634).

Patients on hemodialysis have lower intestinal iron absorption, greater iron losses, and require greater iron turnover to maintain the ESA-driven red cell mass than healthy individuals. In these patients, intravenous iron reduces ESA dose requirements and increases the likelihood of maintaining levels of hemoglobin within the desired range.

Hepcidin excess is one of the main contributors to the disordered iron homeostasis and anemia of CKD which result from impairment of dietary iron absorption and iron mobilization from body stores. (See Babitt et al.).

Iron and EPO are crucial for red blood cell (RBC) production in the bone marrow. Iron availability is controlled by the liver hormone hepcidin, which regulates dietary iron absorption and macrophage iron recycling from senescent red blood cells. There are several feedback loops that control hepcidin levels, including iron and EPO. In CKD patients (particularly in end stage kidney disease patients on hemodialysis), hepcidin levels have been found to be highly elevated, presumably due to reduced renal clearance and induction by inflammation, leading to iron-restricted erythropoiesis. CKD also inhibits EPO production by the kidney, and may also lead to circulating uremic-induced inhibitors of erythropoiesis, shortened red blood cell lifespan, and increased blood loss.

The management of iron deficiency anemia in patients with non-dialysis-dependent chronic kidney disease (NDD-CKD) is controversial, particularly with regard to the use of oral versus intravenous iron supplementation. In practice, oral administration of iron is preferred in patients with NDD-CKD because of its convenience and to avoid systemic adverse events such as hypotension or anaphylactoid reactions.

Iron salts have historically been the most common form of oral iron supplementation used in patients with NDD-CKD. Iron salts exist as the ferrous ($Fe2+$) and ferric ($Fe3+$) forms. For gut absorption, iron must be in the ferrous form; thus, dietary ferric iron is reduced to the ferrous form to be absorbed. Prescribed oral iron salt preparations are in the ferrous form, including ferrous sulfate, ferrous fumarate, ferrous gluconate, and polysaccharide iron complex.

Despite disparities regarding target iron levels and the absence of reliable markers of iron deficiency, the importance of correcting iron deficiency in patients with CKD is indisputable. Oral iron therapies offer safe and effective options to treat iron deficiency anemia in patients with CKD in a physiologic way. In contrast to intravenous iron therapies, oral iron treatments require few resources for administration and are not associated with potential serious adverse events. (Locatelli et al., *Iron Therapy Challenges for the Treatment of Nondialysis CKD Patients*, CLIN. J. AM. SOC. NEPHROL. 2016 Jul. 7; 11(7):1269-80).

The ferrous gluconate of the present invention may provide an excellent opportunity to control the development of renal anemia in patients with chronic kidney disease.

Iron, such as ferrous gluconate, as used in the present invention may be sourced from conventional and commercially available resources.

4. Roundhead *Lespedeza*

*Lespedeza capitata* is a perennial plant belonging to the Fabaceae family (legumes), spread throughout North America, China, Japan and India. The genus *Lespedeza* contains multiple species, including *capitata*.

The active functional components of *Lespedeza capitata* are flavonoids-lespedin (also referred to as kaempferitrin), lespecapitoside, calein and others that are important for glomerular filtration and have a significant effect on renal activity.

The isolated ingredient lespedin (kaempferitin) has a particularly significant effect on various kidney diseases and is associated with improved microcirculation in glomeruli. The group of flavonoids also contains another extremely active ingredient, lespecapitoside. Lespecapitoside acts on the damaged nephron tissue by reducing the overexpression of the nuclear factor KappB and increasing the matrix metalloeotidase 9 (MMP-9) protein expression. The result is a reduction in the extracellular matrix of nephrons.

*Lespedeza capitata* contains proanthocyanidins that have an inhibitory effect on ACE (angiotensin converting enzyme).

The pharmacokinetic properties of *Lespedeza capitata* extract are associated with a concentration of the compounds in the bile. It diffuses into tissues and is eliminated through the urine. In case of renal impairment, a hepatobiliary elimination pathway is used.

As early as the 1950s, *Lespedeza capitata* extracts, given their influence on renal function, were experimentally used to influence renal function in allergic experimental nephritis and to improve diuresis in patients with chronic renal failure. In the 1970s, the flavonoids contained in *Lespedeza* were studied for their ability to control azotemia in patients with renal disease.

The proven advantages of *Lespedeza capitata* are that it helps to eliminate the nitrogenous substances, such as creatinine, urea, uric acid and improves diuresis without altering the electrolyte balance. Another positive effect is that it contributes to the normalization of the lipid profile of the body.

In numerous scientific studies, *Lespedeza capitata* is recommended for one or more of the following: inflammatory kidney disease, chronic kidney failure (CKF), pyelonephritis, glomerulonephritis; as an extremely effective hypoazotemic, as a moderate diuretic that stabilizes water-salt metabolism and acts as an anti-inflammatory; and for recurrent urinary infections and recurrent uroinfections in transplant patients.

Researchers have found that *Lespedeza capitata* has a pronounced hypoazotemic effect, and leads to improvement of diuresis and decrease of the level of residual nitrogen in the blood. It does not cause increased release of potassium from the body.

Researchers have found that *Lespedeza capitata* has extremely low toxicity. In overdoses with very high doses, it is suspected that gastrointestinal irritation or diarrhea may occur. In rare cases, individual hypersensitivity to the extract is possible.

*Lespedeza capitata*'s mechanism of action for removing nitrogen-containing metabolites by improved glomerular filtration, though not yet fully clarified, is thought to be due to lespedine, lespecapitoside, and other *Lespedeza capitata* components that directly affect the vessels and other structures in the glomeruli.

It is reasonably believed that the flavonoids contained in *Lespedeza capitata* are the cause of a possible ACE inhibition that has a moderate diuretic effect.

*Lespedeza capitata* is mainly used for hyperazotemic conditions, subacute and chronic nephropathies, chronic uremia, oliguria, and hypercholesterolemia.

Thus, the present inventors submit that *Lespedeza capitata* imparts one or more of the following attributes to formulations of the present invention: it significantly reduces total vascular resistance of renal afferent and efferent arteries; it decreases the level of nitrogen-containing fractions in blood plasma; it moderately increases urine volume; it contributes to the normalization of acidosis; it increases renal clearance significantly; it maintains the optimal ratio of serum electrolytes; it does not cause increased release of potassium from the body; and, because of its extremely low toxicity, it is suitable for long-term use.

Additionally, the inventors submit that the dry extract of the *Lespedeza capitata* encompassed by the present invention has the advantage over alcohol-containing liquid extract forms due to the disappearance of all contraindications related to the alcohol content. This extends the application range for the present inventive formulations. (Yarnell, E., *Botanical medicines for the urinary tract*, WORLD J. UROL. 2002, November; 20(5):285-93).

In a preferred embodiment, the dry extract of the *Lespedeza capitata* encompassed by the present invention is made from the aerial part of the plant and is characterized by one or more of the following features: (i) appears as a brownish yellow powder; (ii) has a particle sized so that not less than 90% pass through 80 mesh (standard 0.177 mm, nominal sieve opening 0.0070 inches); (iii) has a loss on drying of less than or equal to 5% (w/w), or about 3.30% (w/w); (iv) has a sulfated ash content of less than or equal to 5% (w/w), or about 2.32% (w/w); (v) heavy metals accounting for a total of less than or equal to 10 parts per million (ppm), with arsenic (As) present in an amount less than or equal to 2 ppm, with lead (Pb) present in an amount less than or equal to 2 ppm, with cadmium (Cd) present in an amount less than or equal to 1 ppm, and with mercury (Hg) present in an amount less than or equal to 1 ppm; (vi) a total plate count of less than or equal to 1000 colony forming units (cfu)/gram, or about 90 cfu/g, with yeast and mold present in an amount less than or equal to 100 cfu/g, or less than 10 cfu/g, with *Escherichia coli* (*E. coli*) not present or not detectable, and with *Salmonella* not present or not detectable. Before incorporation into the formulations of the present invention, the dry extract of the *Lespedeza capitata* is stored in a dry cool place in tight containers, protected from strong light and heat.

5. Birch Leaf

Birch leaves were used in ancient Greece. In the Middle Ages, people used birch bark for wound healing. Albrecht von Haller (1708-1777) describes the sudorific and diuretic action of birch juice. In China, birch tea is used to relieve headaches, rheumatic pain and inflammation. In the Baltic republics, birch leaves are a popular means of improving diuresis.

Currently, birch leaves are used in supportive therapy for bacterial and inflammatory diseases of the kidneys and urinary tract and for increasing the amount of urine. In France, birch tea is traditionally used to improve the urinary and digestive functions of the body and enhance the diuretic effect. In Germany it is used in inflammation and urinary tract infections. A monograph on *Betulae folium* (birch leaf) is published in the European Pharmacopoeia.

The birch leaves contain 1-3% flavonol glycosides, mainly hyperoside and others, quercetin (3,5,7,3',4'-pentahydroxyl-flavone) glycosides, kempferol (7-tetra-hydroxyl-flavone) glycosides, and myricetin.

Other phenolic components include: 3,4 dihydroxypropiophenone 3-glucoside, caffeic acid, and chlorogenic acid. Also included, are triterpene alcohol malonyl esters, saponins, and tannins.

The content of flavonoids in birch leaf specimens ranges from 2% to 3.5%, calculated as hyperosides.

In recent years, the following flavonoids have been confirmed in the birch leaf: quercetin-3-O-galactoside (also known as hyperoside), quercetin-3-O-glucuronide, myricetin-3-O-galactoside, and quercetin-3-rhamnoside, as well as other quercetin glycosides (Hänsel R, Sticher O. (eds.) PHARMAKOGNOSIE—PHYTOPHARMAZIE Springer: Berlin, Heidelberg (2010)).

The flavonoids found in birch leaves are mainly polymeric proanthocyanidins.

Very detailed studies have been published on the content of flavonoids in dry birch leaves. The analyses show: total flavonoids of 2 to 3.5%, including hyperoside, avicularin, galactosyl-3-myricetol, glucuronyl-3-quercetol, and quercitrin. (Karonen, M. et al. *Quantitative analysis of polymeric proanthocyanidins in birch leaves with normal-phase HPLC,* PHYTOCHEM. ANAL., 17, 2006, No 3, 149-156; Lahtinen, M. et al., *HPLC analysis of leaf surface flavonoids for the preliminary classification of birch species,* Phytochem. Anal., 17, 2006, No 3, 197-203; V. Ossipov et al, *High-performance liquid chromatographic separation and identification of phenolic compounds from leaves of Betula pubescens and Betula pendula,* J. CHROMATOGR. A, 721, 1996, No 1, 59-68; and Wang, S. J. et al., *A new monoterpene glucoside from the leaves of Betula platyphylla Suk,* CHIN. CHEM. LETTERS, 12, 2001, No 4, 343-344)).

Whereas, in the past, the diuretic effect of birch leaves was thought to be due to betulin, which is a terpene alcohol, in later studies it was found that flavonoids, such as hyperoside (quercitol-3-galactoside), are important ingredients that are at the root of the mechanism of action. Flavonoids have the ability to accelerate renal blood flow, thus improving glomerular filtration. This is due to endothelial dependent vasorelaxation due to increased production of nitrogen (NO) without altering the production of oxygen ($O_2$). This leads to increased bioavailability of nitrogen (NO) and activation of the NO-cGMP metabolic pathway.

Glucoside flavonoids act on the proximal sites of Henle's loop and the distal and collecting canals by increasing the osmotic pressure in their lumen. Some flavonoids block the Cl⁻ channels for chlorine ions in the epithelial cells of the distal and collecting canals. This leads to an increase in the intraluminal negative charge and suppression of the reverse resorption of (Na) sodium.

It is known that flavonoids are synthesized in plants in response to microbial infection. They exhibit antimicrobial activity against a broad spectrum of microorganisms. Flavonoids such as hyperoside, myricitroside, and quercetin are supposed to inhibit the tyrosine kinase of the infection inducers. The flavonoids interact with the nucleophilic amino acids of the cell membrane proteins of the pathogenic bacteria. They most often interact with surface adhesin polypeptides from the cell wall and membrane-bound enzymes. It is known that hyperoside and quercetin inhibit mast cell degranulation, probably by intracellular cyclic to cATP and direct membrane stabilizing activity, and thus inhibit histamine release.

Quercetin suppresses the release of leukotrienes and other prostaglandin precursors. The antibacterial effect may also be due to suppression of gene expression in some pathogenic microorganisms. Kobuchi et al., *Quercetin inhibits inducible ICAM*-1 *expression in human endothelial cells through the JNK pathway,* AM. J. PHYSIOL., 1999 September; 277(3 Pt 1):C403-11.

The physiological action of tannins is expressed in stimulating phagocytosis and cell mediated immunity as well as in antibacterial activity due to their ability to form hydrophobic, hydrogen and covalent bonds with proteins from the cell wall and cell membrane of the microorganisms. Tannins also form complexes with the cell wall polysaccharides. The antimicrobial properties of tannins were summarized by Scalbert in 1991. He cited 33 studies that documented the inhibitory activity of tannins. According to these studies, tannins are toxic to certain filamentous fungi, yeasts and bacteria. (Scalbert, A., *Antimicrobial properties of tannins,* PHYTOCHEMISTRY, Volume 30, Issue 12, 1991, pp. 3875-3883).

Numerous studies have shown antibacterial activity in the triterpenes, although their mechanism of action has not been fully studied. Their action is believed to be due to cell membrane destruction caused by the lipophilic properties of triterpene molecules.

The birch extract is mainly associated with its anti-inflammatory action and moderate diuretic effect. The increase in diuresis is due to potassium nitrate and flavonoids found in birch leaves. The litholytic action of birch leaf extract is mainly determined by flavonoids, such as quercitrin and hyperoside, which act on a number of enzyme systems that modulate P-glycoprotein, cytochrome enzymes and MRP protein.

In a preferred embodiment, the dry birch leaf extract (botanical source *Betula platyphylla* Suk.) encompassed by the present invention is characterized by one or more of the following features: (i) appears as a brownish yellow powder; (ii) has a particle sized so that not less than 95% pass through 80 mesh (standard 0.177 mm, nominal sieve opening 0.0070 inches); (iii) has a loss on drying of less than or equal to 5% (w/w), or about 3.58% (w/w); (iv) has a sulfated ash content of less than or equal to 5% (w/w), or about 3.16% (w/w); (v) heavy metals accounting for a total of less than or equal to 10 parts per million (ppm), or about 1.55 ppm, with arsenic (As) present in an amount less than or equal to 2 ppm, or about 0.08 ppm, with lead (Pb) present in an amount less than or equal to 2 ppm, or about 0.56 ppm, with cadmium (Cd) present in an amount less than or equal to 1 ppm, or about 0.03 ppm, and with mercury (Hg) present in an amount less than or equal to 1 ppm, or about 0.05 ppm; (vi) a total plate count of less than or equal to 1000 colony forming units (cfu)/gram, or about 300 cfu/g, with yeast and mold present in an amount less than or equal to 100 cfu/g, or less than 20 cfu/g, with *Escherichia coli* (*E. coli*) not present or not detectable, and with *Salmonella* not present or not detectable. Before incorporation into the formulations of the present invention, the dry birch leaf extract is stored in a dry cool place in tight containers, protected from strong light and heat.

6. Red Bilberry

Red bilberry, cranberry, and blueberry are closely related members of the *Vaccinium* genus. For centuries, North American Indians have used cranberries as a medicine. As early as 300 years ago, they began to use these fruits as an anti-inflammatory agent for wound healing and pain relief. Today, cranberry is known for its numerous health effects. Of particular importance is the ability of cranberry to prevent urinary tract infections due to its unique antibacterial effect. The berries are rich in vitamins, trace elements, minerals, tannins, flavonoids, and essential fatty acids, such as linoleic acid (omega 6), alphalinoleic acid (omega 3), carotenoids, and phytosterols.

Cranberries contain about 6% arbutein, traces of hydroquinone, and about 8% catechinic tannins, flavonoids like quercetin, hyperoside, isoquercetin, ursolic and chlorogenic acids, and vitamins C, A, and E. Cranberries are found to contain tocotrienol, the rarest form of vitamin E. This antioxidant is 40 to 60 times more effective than tocopherol, the most common form of vitamin E. Of all natural oils, cranberry oil contains the largest amount of tocotrienol. Cranberries are also remarkable for containing large quantities of iron, as well as having a low glycemic index. (He et al., *Cranberry phytochemicals: isolation, structure elucidation, and their antiproliferative and antioxidant activities*, J. AGRIC. FOOD CHEM., 54, 2006, 7069-7074; Sobota, A. E., *Inhibition of bacterial adherence by cranberry juice: potential use for the treatment of urinary tract infections*, J. UROL., 1984 May 131(5):1013-1016).

Cranberries, a member of the *Vaccinium* genus, are a rich and heterogeneous source of phytochemicals. Over 150 different individual phytochemicals have been identified and studied in cranberries, and many more may be discovered with continued improvements in analytical methods. By far, the dominant components are flavonoids. Most readily recognized are anthocyanins, responsible for the bright red cranberry color; flavonols, secondary yellowish pigments; proanthocyanidins associated with protection against urinary tract infections; catechins, organic acids, and resveratrol which contribute the sour, astringent flavor unique to cranberries; terpene aroma components; and pectins, that gel cooked cranberries into cranberry sauce. Most research has focused on cranberry flavonoids, including anthocyanins (ACYs), proanthocyanidins (PACs), flavonols, and flavan-3-ols. Other polyphenolics, simple phenolics, terpenes, organic acids, complex carbohydrates, and sugars of cranberries have attracted somewhat less medical research attention, but nevertheless have shown some promise as health promoters. (Pappas, E. and Schaich, K. M. *Phytochemicals of cranberries and cranberry products: characterization, potential health effects, and processing stability*, CRIT. REV. IN FOOD SCI. NUTR., 2009 49(9): 741-781).

The type A proanthocyanidins contained in the cranberry reduce the adhesion ability of pathogenic bacteria. Thus, the bacteria lose the ability to adhere to uroepithelial cells. The virulence of a number of pathogenic *E. coli* strains is due to their expressed adhesins, type P and type 1 fimbriae, by which they are attached to specific uroepithelial cell receptors because the immune system does not recognize *E. coli* as pathogenic. In contrast, proanthocyanidins type A recognize *E. coli*, preventing its binding to receptors on the surface of the urinary tract. Due to inhibition of this relationship, the bacteria fail to attach and are "transported" through the urine outside the body. Thus, bacteria can affect neither the urinary tract nor the bladder. Type A proanthocyanidins destroy only the bond of the pathogenic bacteria to the receptors without destroying the entire *E. coli* population, some strains of which are part of the beneficial microflora in the gut. Proanthocyanidins (PACs) are widespread in plants, but a number of clinical studies show that only so-called A-type PACs in cranberries have antiadhesive effect. (Pappas et al., *Phytochemicals of cranberries and cranberry products: characterization, potential health effects, and processing stability*, CRIT. REV. FOOD SCI. NUTR., 49, 2009, 741-781; Lowe et al., *Cranberry juice and urinary tract infections: what is the evidence?*, UROLOGY, 57, 2007, 407-413).

In many clinical trials, morphological changes have been identified in uropathogenic *E. coli* under the influence of Type A proanthocyanidins (PACs) and the other ingredients of cranberry extract. In addition to adhesion inhibition, bacterial cell prolongation, and shortening and loss of fimbriae are observed. After treatment with cranberry fruit extract, the length of *E. coli* HB101pDC1 fimbriae decreases nearly three times from 148 nm to 48 nm. (Liu, Y. et al., *Role of cranberry juice on molecular-scale surface characteristics and adhesion behavior of Escherichia coli*, BIOTECHNOL. BIOENG., 2006 Feb. 5; 93(2):297-305)

Because of these properties, cranberry is used in inflammation, stones in the urinary tract, cystitis, etc., as an anti-inflammatory agent.

The main effect of the intake of cranberry is that it is extremely effective in treating problems, disorders and diseases of the excretory system. Further, due to the substrates contained in the cranberry, it has a very good antiseptic, anti-inflammatory, and antioxidant effect for the whole excretory system.

In a preferred embodiment, the dry red bilberry extract encompassed by the present invention is made from the fruit part of the plant (*Vaccinium hirtum* Thunb), uses ethanol and water as extract solvents, and is characterized by one or more of the following features: (i) appears as a purple red fine powder; (ii) has a particle sized so that not less than 95% pass through 80 mesh (standard 0.177 mm, nominal sieve opening 0.0070 inches); (iii) has a loss on drying equal to about 5% (w/w), or about 3.02% (w/w); (iv) has a sulfated ash content equal to about 5% (w/w), or about 1.76% (w/w); (v) a pH (1% water solution) of about 3.38; (vi) heavy metals accounting for a total of less than or equal to 20 parts per million (ppm), with arsenic (As) present in an amount less than or equal to 2 ppm, with lead (Pb) present in an amount less than or equal to 3 ppm, and with mercury (Hg) present in an amount less than or equal to 0.1 ppm; (vii) a total plate count of less than or equal to 1000 colony forming units (cfu)/gram, with yeast and mold present in an amount less than or equal to 100 cfu/g, with *Escherichia coli* (*E. coli*) not present or not detectable, with *Salmonella* not present or not detectable, and with *Staphylococcus* not present or not detectable. Before incorporation into the formulations of the present invention, the dry red bilberry fruit extract is stored in a cool place protected from sun light.

Manufacture

In a preferred embodiment, the aforementioned active substances are mixed in a stainless reactor in the aforementioned ratios, auxiliary substances to facilitate processing are added, and the resulting mixture is homogenized to obtain a homogeneous product. In another preferred embodiment, the aforementioned active substances are mixed in a stainless reactor in the aforementioned ratios as dry (e.g., less than or equal to 5% (w/w) water, less than or equal to 4% (w/w) water, less than or equal to 3% (w/w) water, less than or equal to 2% (w/w) water, less than or equal to 1% (w/w) water, less than or equal to 0.5% (w/w) water, or less than or equal to 0.1% (w/w) water) components or extracts, auxiliary substances are added, and the resulting mixture is homogenized to obtain a homogeneous dry powder.

In an alternative embodiment, inactive components are added and homogenized along with the active substances and/or auxiliary substances. Inactive components (which may or may not be auxiliary substances) such as, for example, microcrystalline cellulose, polyvinylpyrrolidone, magnesium stearate, talc, and film coating (e.g., polyvinyl Alcohol, titanium dioxide color, polyethylene glycol, and talc), may be used to stabilize the formulation active agents.

In certain embodiments, the inventive formulations described herein include microcrystalline cellulose, polyvinylpyrrolidone, magnesium stearate, talc, and film coating (e.g., polyvinyl Alcohol, titanium dioxide color, polyethylene glycol, and talc). The inventors note, however, that the selection of excipients used with the invention described herein may vary. In one embodiment, specific technological processes may be guaranteed by GMP, HACCP, ISO and EU certificate of conformity.

A preferred embodiment of the present invention uses Nutraficient® (made by Colorcon® company), a food supplement coating designed as an immediate release coating system specifically for nutritional, herbal and dietary supplements. This coating may be used for tablet formulations and not only provides moisture protection but also helps overcome unpleasant tastes and odors.

In a preferred embodiment, the mixture is dispensed into capsules. The capsules may be formed from hydroxypropyl methylcellulose, pullulan, gelatin, starch, cellulose, or any other appropriate material. In a preferred embodiment, the capsules are formed from hydroxypropyl methylcellulose, such as the Vcaps® Plus capsule manufactured by Capsugel®. The capsules used may eliminate the need for gelling systems and may disintegrate and release their contents independent of pH and ionic strength of the test medial. The capsules used may provide immediate release in-vivo performance bioequivalent to gelatin and consistent dissolution across changing pH and ionic strength. The capsules used may help maintain the stability of the active agent payload by preventing moisture transfer from the capsule to the encapsulated product. Capsules of the present invention may also provide moisture protection and help overcome unpleasant tastes and odors, and also facilitates swallowing, as the products and methods of the present invention may be taken or practiced for a long time.

In a preferred embodiment, a dosage form may be a capsule and may contain the following biologically active substances: about 4 mg vitamin $B_6$ (pyridoxine HCl), about 9 mg vitamin E (natural d-α-tocopherol; 10 IU), about 6 mg iron (as ferrous gluconate), about 280 mg dry extract of roundhead *Lespedeza* (stem and leaf, comprising lespedine and lespecapitoside), about 250 mg dry extract of birch leaf (leaf), and about 100 mg dry extract of red bilberry (*Vaccinium hirtum* Thunb.) (fruit). In another embodiment, a dosage form may be a capsule and may contain the following biologically active substances: about 4 mg vitamin $B_6$ (pyridoxine HCl), about 9 mg vitamin E (natural d-α-tocopherol; 10 IU), about 6 mg iron (as ferrous gluconate), about 250 mg dry extract of roundhead *Lespedeza* (stem and leaf, comprising lespedine and lespecapitoside), about 250 mg dry extract of birch leaf (leaf), and about 100 mg dry extract of red bilberry (*Vaccinium hirtum* Thunb.) (fruit).

Dosage forms, such as capsules according to the present invention are generally expected to be greater than 500 mg in weight. In a preferred embodiment, the weight of the dosage forms described herein ranges from about 500 mg to about 850 mg without the capsule, and from about 700 mg to about 1050 mg with the capsule. For example, the weight of the dosage forms described herein, without the capsule, may range from about 500 mg to about 550 mg, from about 500 mg to about 600 mg, from about 500 mg to about 650 mg, from about 500 mg to about 700 mg, from about 500 mg to about 750 mg, from about 500 mg to about 800 mg, from about 500 mg to about 850 mg, from about 550 mg to about 600 mg, from about 550 mg to about 650 mg, from about 550 mg to about 700 mg, from about 550 mg to about 750 mg, from about 550 mg to about 800 mg, from about 550 mg to about 850 mg, from about 600 mg to about 650 mg, from about 600 mg to about 700 mg, from about 600 mg to about 750 mg, from about 600 mg to about 800 mg, from about 600 mg to about 850 mg, from about 650 mg to about 700 mg, from about 650 mg to about 750 mg, from about 650 mg to about 800 mg, from about 650 mg to about 850 mg, from about 700 mg to about 750 mg, from about 700 mg to about 800 mg, from about 700 mg to about 850 mg, from about 750 mg to about 800 mg, from about 750 mg to about 850 mg, or from about 800 mg to about 850 mg; and the weight of the dosage form described herein, with the capsule, may range from about 700 mg to about 750 mg, from about 700 mg to about 800 mg, from about 700 mg to about 850 mg, from about 700 mg to about 900 mg, from about 700 mg to about 950 mg, from about 700 mg to about 1000 mg, from about 700 mg to about 1050 mg, from about 750 mg to about 800 mg, from about 750 mg to about 850 mg, from about 750 mg to about 900 mg, from about 750 mg to about 950 mg, from about 750 mg to about 1000 mg, from about 750 mg to about 1050 mg, from about 800 mg to about 850 mg, from about 800 mg to about 900 mg, from about 800 mg to about 950 mg, from about 800 mg to about 1000 mg, from about 800 mg to about 1050 mg, from about 850 mg to about 900 mg, from about 850 mg to about 950 mg, from about 850 mg to about 1000 mg, from about 850 mg to about 1050 mg, from about 900 mg to about 950 mg, from about 900 mg to about 1000 mg, from about 900 mg to about 1050 mg, from about 950 mg to about 1000 mg, from about 950 mg to about 1050 mg, or from about 1000 mg to about 1050 mg.

Due to size constraints or to facilitate ease of administration, the inventors also contemplate that the dosage forms used to deliver an effective amount of the compositions of the present invention may be divided or delivered between two, three, four, five, etc. dosage forms such as capsules at each oral dosing. In a preferred embodiment, the daily intake is three capsules or tablets.

In an alternative embodiment, the mixture is compressed into tablets. The tablets are a homogeneous mixture, granulated, compressed and film coated. The mixture may be directly compressed in a single compression and may or may not involve heat compression. The tablets may be film coated to avoid bad taste and to facilitate swallowing as the products and methods of the present invention may be taken or practiced for a long time.

In an alternative embodiment, dosage forms, such as tablets, according to the present invention are generally expected to be greater than 550 mg in weight. In a preferred embodiment, dosage forms, such as tablets, according to the present invention are expected to be equal to or greater than about 850 mg and weight. In another preferred embodiment the weight of the dosage forms described herein ranges from about 700 mg to about 950 mg. For example, the weight of the dosage forms described herein by range from about 700 mg to about 750 mg, from about 700 mg to about 800 mg, from about 700 mg to about 850 mg, from about 700 mg to about 900 mg, from about 700 mg to about 950 mg, from about 750 mg to about 800 mg, from about 750 mg to about 850 mg, from about 750 mg to about 900 mg, from about 750 mg to about 950 mg, from about 800 mg to about 850 mg, from about 800 mg to about 900 mg, from about 800 mg to about 950 mg, from about 850 mg to about 900 mg, from about 850 mg to about 950 mg, or from about 900 mg to about 950 mg. Also, the inventors contemplate that the dosage forms used to deliver an effective amount of the compositions of the present invention may be divided or delivered between two, three, four, or five, etc., dosage forms such as tablets at each oral dosing.

The following machinery and equipment may be used to make the compositions of the present invention: a stainless steel mixer, a capsule-filling machine or tableting machine, a filming machine, auxiliary equipment, electromagnets for induction sealing, a machine for heat shrink film, and an inkjet printer.

Basic and additional raw materials contemplated for use with the present invention include raw materials produced in regulated plants subject to all technological and hygienic standards and requirements, accompanied by documents of origin and suitability, are used for the production.

In one particularly preferred embodiment, the active agents of a dosage form of the present invention comprises, consists essentially of, or consists of, dry extract of roundhead Lespedeza (aerial part of the plant) in the amount of about 280 mg, dry extract of birch leaf in the amount of about 250 mg, dry extract of red bilberry fruit in the amount of about 100 mg, vitamin B6 in the amount of about 4 mg, vitamin E in the amount of about 10 IU (9 mg), iron in the amount of about 6 mg, and a hydroxypropyl methylcellulose capsule weighing about 163 mg, for a total capsule weight of about 812 mg.

In an alternative embodiment, the active agents of a dosage form of the present invention comprises, consists essentially of, or consists of, dry extract of roundhead Lespedeza (aerial part of the plant) in the amount of about 250 mg, dry extract of birch leaf in the amount of about 250 mg, dry extract of red bilberry fruit in the amount of about 100 mg, vitamin $B_6$ in the amount of about 4 mg, vitamin E in the amount of about 10 IU (9 mg), iron in the amount of about 6 mg, and a hydroxypropyl methylcellulose capsule weighing about 163 mg, for a total capsule weight of about 782 mg.

In a preferred embodiment, the manufacturing process of the product includes the following phases: (1) weighing active substances according to the one-capsule rate; (2) mixing and homogenization in a stainless steel mixer; (3) granulation by (a) humidification of the mixed active substances by water-alcohol solution, (b) drying at temperatures up to 40° C., (c) sieving the dried mixture; (4) dosing and dispensing of the product into capsules via a capsule-filling machine; (5) sorting and separation of technological waste after performing item 4 of the technological process—maximum allowed up to 10%—as a result of spills, dusting, adjustments and defects during operation; (6) counting and filling in bottles; (7) placing a thermo shrink film; and (8) printing the markings by using an inkjet printer.

In an alternative embodiment, a dosage form of the present invention includes the addition of the following excipients: microcrystalline cellulose in the amount of about 121 mg, polyvinylpyrrolidone in the amount of about 35 mg, magnesium stearate in the amount of about 5 mg, talc in the amount of about 10 mg, and film coating in the amount of about 30 mg, which combined with 649 mg of active agents, result in a total tablet weight of about 850 mg. In yet another alternative embodiment, a dosage form of the present invention includes the addition of the following excipients: microcrystalline cellulose in the amount of about 151 mg, polyvinylpyrrolidone in the amount of about 35 mg, magnesium stearate in the amount of about 5 mg, talc in the amount of about 10 mg, and film coating in the amount of about 30 mg, which combined with 619 mg of active agents, result in a total tablet weight of about 850 mg. As noted above, it is contemplated by the inventors that payload delivery of the active ingredients may be accomplished using only one dosage form per administration, or by using multiple dosage forms wherein the payload of active ingredients is divided between the multiple dosage forms.

In one embodiment, the manufacturing process of the product includes the following phases: (1) weighing excipients and active substances according to the one-tablet rate; (2) mixing of the excipients with the active substances and homogenization in a stainless steel mixer; (3) granulation by (a) humidification of the mixed active substance by water-alcohol solution, (b) drying at temperatures up to 40° C., (c) sieving the dried mixture, and (d) input of excipients in the active mixture; (4) dosing and tableting of the product via a tablet machine; (5) filming of the tablets by means of a filming machine (30 to 40% technological loss due to the volatility of the material); (6) sorting and separation of technological waste after performing items 4 and 5 of the technological process—maximum allowed up to 10%—as a result of spills, dusting, adjustments and defects during operation; (7) counting and filling in bottles; (8) placing a thermo shrink film; and (9) printing the markings by using an inkjet printer.

EXAMPLES

Example 1

Clinical trial with compositions similar to those of the present invention, but excluding and without the added benefit of vitamin $B_6$, vitamin E, and iron, in patients with initial renal insufficiency.

At the Multispecialty Hospital for Active Treatment in Plovdiv, Bulgaria, under the guidance of Professor Dimitar Dimitrakov, patients with initial renal insufficiency (creatinine up to 360 mmol/l and creatinine clearance of 40-20 ml) were studied. Of these, 60% were women and 40% were men aged 26-70 years. A formulation comprising 250 mg Lespedeza capitata extract, 250 mg birch leaf extract, and 100 mg red bilberry extract was given at a dose of one tablet 3 times per day, half an hour before meals.

The dynamics of the nitrogen-containing urea and creatinine as well as creatinine clearance were monitored at the beginning, during, and after completion of the study, as well as the liver enzymes and the lipid profile, specifically cholesterol, triglycerides, and low density lipoproteins.

Analysis of the data obtained after completion of clinical observation showed a significant decrease of the nitrogen-containing indicators: urea, creatinine, and uric acid.

To assess the effect on renal function, particularly indicative was the increase in creatinine clearance, which changed from 37.14 ml/min to 42.17 ml/min. The same trend is also observed for triglycerides, which changed from 1.6 mol/l before starting treatment to 1.41 mol/l. There was no change in sodium serum levels, whereas potassium had a decrease in serum levels but it remains within the normal range.

These results confirmed a positive impact of the tested formulation in several important ways: (1) positive cleansing action of nitrogen-containing products; (2) improvement of kidney excretory function, which is demonstrated by an increase in creatinine clearance; (3) anti-gout action by lowering uric acid; (4) diuretic effect by increasing glomerular filtration; (5) reduces blood pressure through increased diuresis; and (6) possible inhibition of angiotensin converting enzyme (ACE).

The following conclusions were made. First, due to its natural origin, the tested formulation had excellent tolerance and was practically harmless, such that it may be used in a prolonged administration for one to several months, without the risk of negative effects on other organs and tissues. Second, side effects were not identified in the observed patients. At higher doses, it is possible to expect gastroenterological symptoms such as nausea and epigastric pain, but these effects are rare in these optimal values. Accordingly, it was determined that the tested formulation can be used in initial chronic kidney failure under dietary conditions having a limitation of protein intake. The positive changes recorded during laboratory tests during the study proved its effect in the event of chronic kidney failure. Further, the properties of the active ingredients enhance the kidney detoxifying function.

Example 2

Clinical trials were conducted with compositions similar to those of the present invention, but excluding vitamin $B_6$, vitamin E, and iron, in renal transplant patients with recurrent uroinfections.

A clinical trial was conducted at the Clinic of Nephrology and Transplantation at the Alexandrovska University Hospital in Sofia, Bulgaria.

The study included renal transplant recipients with recurrent uroinfections observed in the Clinic of Nephrology and Transplantation at the Alexandrovska University Hospital for a period of six months of one calendar year, from Mar. 1, 2013 to Aug. 31, 2013. Of the total number of patients, 63% were women and 37% were men aged 24 to 65, averagely 44.5 years old. The average duration of transplantation in months is 41+/−9. A control group of non-transplanted patients with recurrent uroinfections of the same characteristics was also examined.

Patients received a formulation comprising 250 mg *Lespedeza capitata* extract, 250 mg birch leaf extract, and 100 mg red bilberry extract in 2 tablets, twice a day for the first month and 1 tablet, twice a day for the remaining months. The treatment was both outpatient and inpatient, depending on the specific cases and respective indications.

The results found that the tested formulation led to an increase in the cleansing functions of the kidneys both in transplanted and non-transplanted patients, resulting in significant decreases in serum creatinine and urea, and increase in creatinine clearance. Also, in the majority of patients treated, the tested formulation was shown to have antibacterial and antiseptic effect in the treatment of uroinfections in renal transplant patients and in non-transplant recipients with recurrent uroinfections. Further, the use of the tested formulation led to a reduction in the incidence of recurrence of urinary infections in 87% of the kidney transplant patients and in 76.7% of the control group.

These results lead the researchers to conclude that the tested formulation improves the excretory function of the transplanted kidney, which is demonstrated by an increase in creatinine clearance, has a pronounced antiuricemic effect by lowering uric acid values, reduces the frequency of urinary infections and their recurrence in kidney transplanted recipients and non-transplanted patients suggests that the tested formulation should be used successfully in transplant patients receiving immunosuppressive therapy, and that the tested formulation does not show side effects in patients, i.e. it has excellent tolerability and can be used long-term in transplanted and non-transplanted patients.

In all, it was found that the tested formulation contributed to slowing the development of the main kidney disease, helped to slow the progression of chronic kidney failure in the initial and advanced stages and delayed the incidence of patients on hemodialysis treatment. The nephroprotective action of the tested formulation made it suitable for use in patients undergoing chemotherapy both during and after medication courses.

Additionally, the unique properties of the tested formulation as a natural corrector of various cell-level exchange processes and release of the body from various metabolic waste products make it widely applicable either on its own or as part of conventional treatment in chronic kidney disease (CKD) (e.g., pyelonephritis, glomerulonephritis), metabolic diseases (e.g., gout, diabetic nephropathy); chronic kidney failure (CKF) in early and advanced stages; chronic kidney damage in kidney-stone disease; infections of the urinary system (e.g., cystitis); and renal impairment during and after chemotherapy. (B. Zlatkov, Zh. Filipov, E. Paskalev, B. Markova, Yu. Marteva-Proevska, A. Kolevski, Clinic of Nephrology and Transplantation, UMHAT "Aleksandrovska"—Sofia, Central Laboratory of Microbiology, UMHAT "Aleksandrovska"—Sofia; Use Of Renohelp M In Patients With Recurrent Urinary Tract Infections; Medical Review, 50, 2014, No. 2, 35-39).

Example 3

Clinical trials were conducted with compositions of the present invention, but excluding vitamin $B_6$, vitamin E, and iron, in patients with chronic kidney disease.

A clinical trial was conducted at the Clinic of Nephrology and Transplantation at the Alexandrovska University Hospital in Sofia, Bulgaria. A tablet formulation comprising 280 mg *Lespedeza capitata* extract, 250 mg birch leaf extract, 100 mg red bilberry extract, 4 mg vitamin $B_6$ (pyridoxine HCl), 9 mg vitamin E (D-alpha tocopherol), and 6 mg iron (ferrous gluconate) was given 3 times per day with a one tablet dose, half an hour before meals.

The study included 30 patients (15 men and 15 women) and lasted for three months. Measurements of serum creatinine, glomerular filtration (GF), urea, ruic acid, cholesterol, triglycerides, glutamate oxalate transaminase (GOT), glutamate pyruvate transaminase (GPT), alkaline phosphates (AF), gamma glutamyl transpeptidase (GGTP), bilirubin, blood sugar, potassium, sodium, blood count, iron, iron binding capacity and blood pressure were carried out at the beginning of the study, after two months, and after three months. A urine culture test and an assessment for side effects were also done at these time points. Table 2 shows select measurements taken before the study.

TABLE 2

| M:F | 1:1 |
|---|---|
| Average age (years) | 47 ± 6 |
| Average GF (ml/min) | 56 ± 12 |
| Mean value of creatinine (µmol/l) | 157 ± 18 |
| Average uric acid (µmol/l) | 432 ± 27 |
| Hemoglobin (g/l) | 112 ± 5 |
| Average blood pressure (mmHg) | 145(±10)/85(±15) |
| Average cholesterol (mmol/l) | 6.5 ± 0.7 |
| Serum iron (µmol/l) | 14.5 ± 5 |

The change in hemoglobin levels is shown in FIG. 1. Hemoglobin levels tended to increase over the course of the study.

Figure 2:
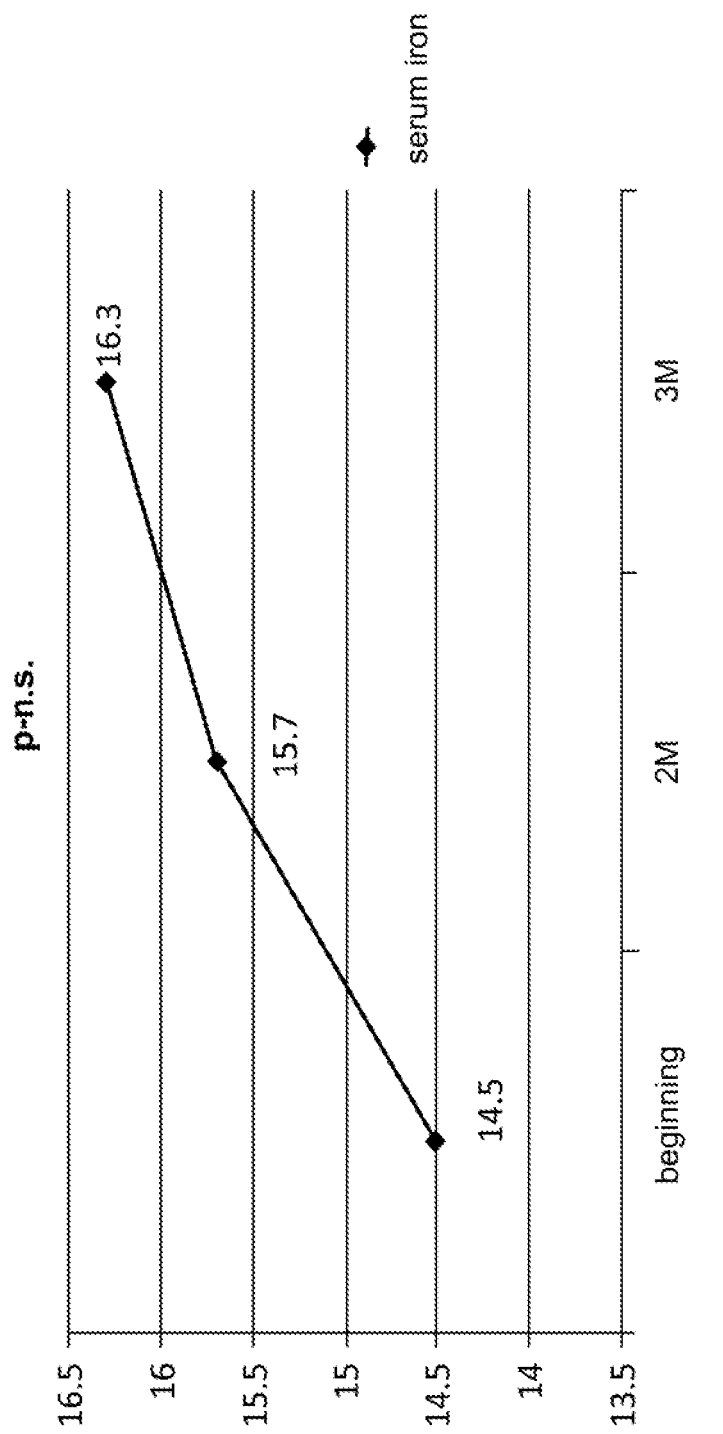
FIG. 2 illustrates the average serum iron level of the study patients measured at the beginning of the study, after 60 days ("2M"), and at the end of the study after 90 days ("3M"), shown μmol/l.

The change in serum iron levels is shown in FIG. 2. Serum iron levels tended to increase over the course of the study.

Figure 3:
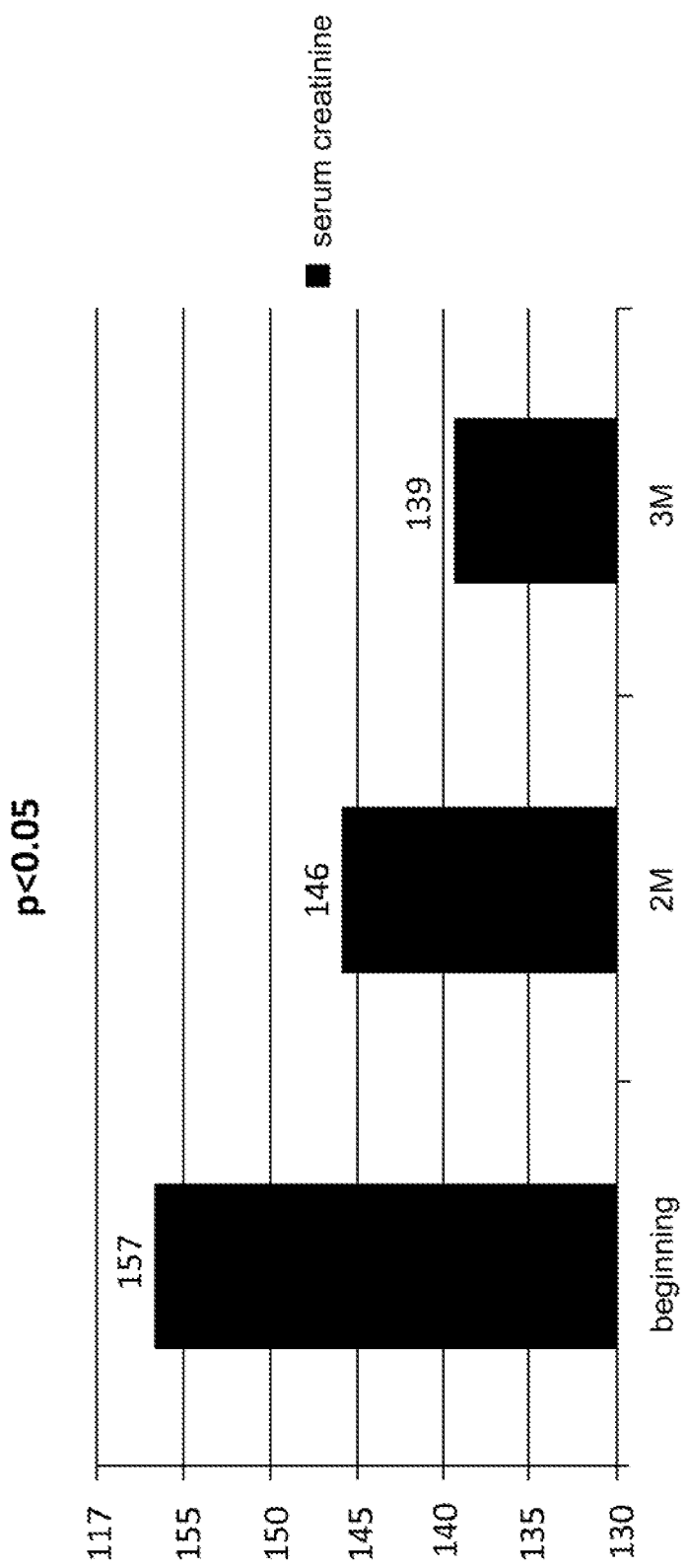
FIG. 3 illustrates the average serum creatinine level of the study patients measured at the beginning of the study, after 60 days ("2M"), and at the end of the study after 90 days ("3M"), shown μmol/l.

The change in serum creatinine levels is shown in FIG. 3. The tested product significantly improved renal function over the course of the study, with $p<0.05$.

Figure 4:
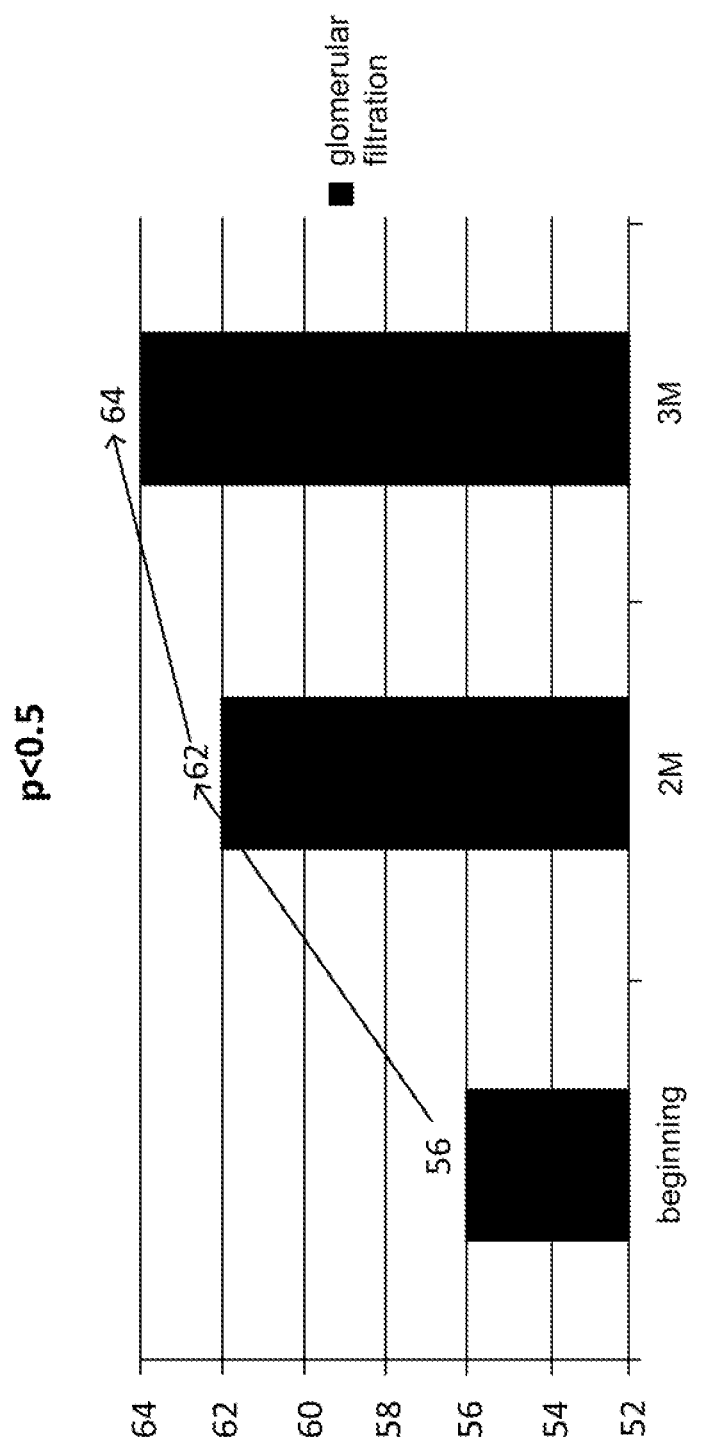
FIG. 4 illustrates the average glomerular filtration of the study patients measured at the beginning of the study, after 60 days ("2M"), and at the end of the study after 90 days ("3M"), shown in ml/min.

The change in glomerular filtration is shown in FIG. 4. The tested product significantly improved glomerular filtration over the course of the study, with $p<0.5$.

Figure 5:
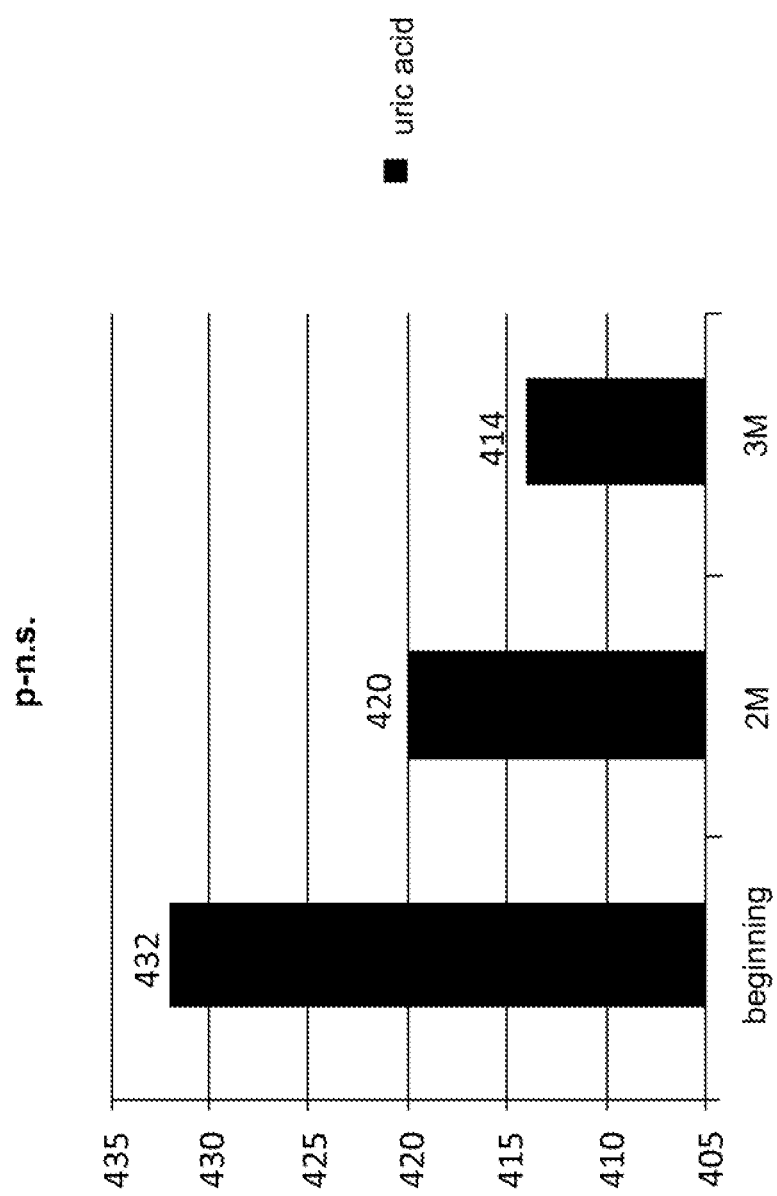
FIG. 5 illustrates the average uric acid level of the study patients measured at the beginning of the study, after 60 days ("2M"), and at the end of the study after 90 days ("3M"), shown μmol/l.

The change in uric acid levels is shown in FIG. 5. Uric acid levels tended to decrease over the course of the study.

Figure 6:
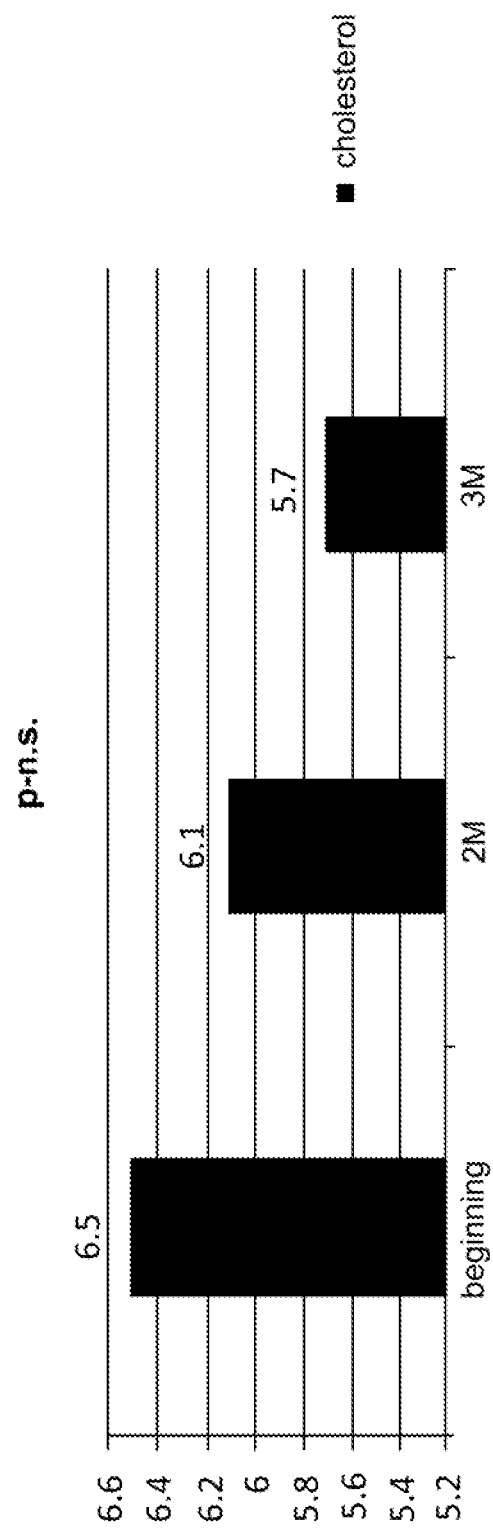
FIG. 6 illustrates the average cholesterol level of the study patients measured at the beginning of the study, after 60 days ("2M"), and at the end of the study after 90 days ("3M"), shown in mmol/l.

The change in cholesterol levels is shown in FIG. 6. Cholesterol levels tended to decrease over the course of the study.

Figure 7:
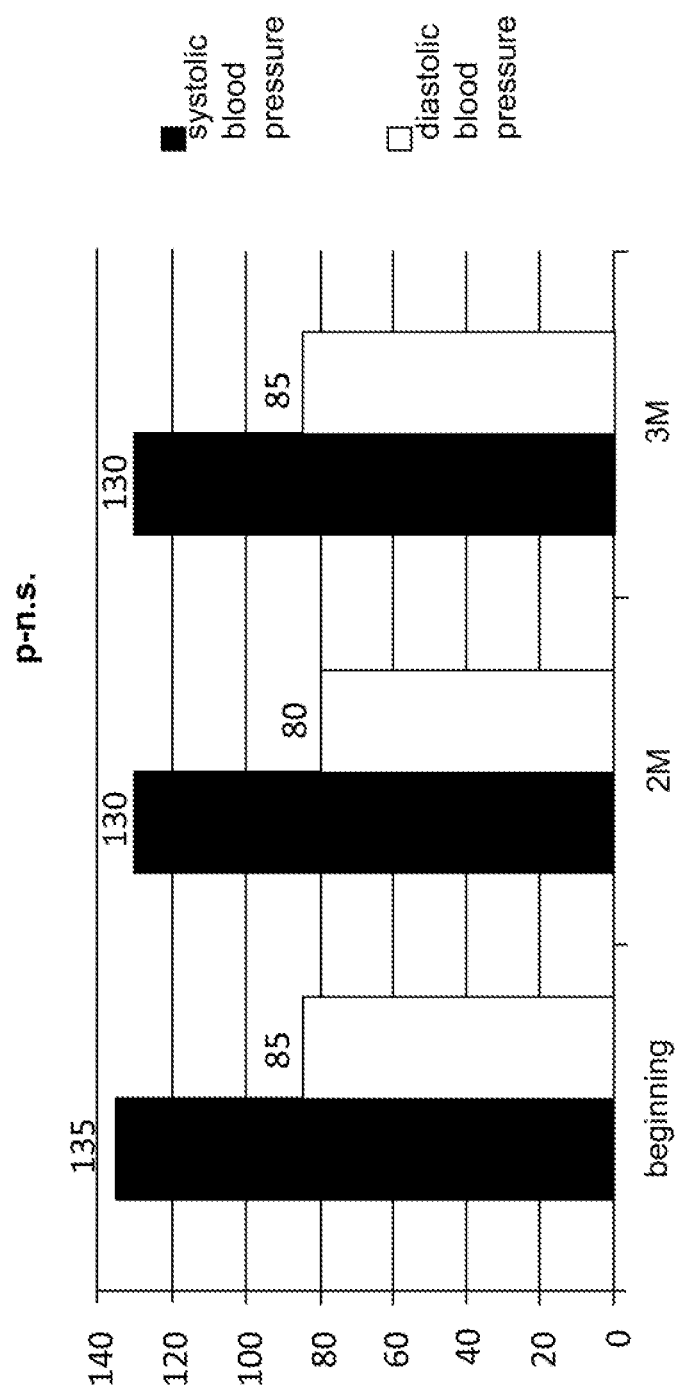
FIG. 7 illustrates the average systolic and diastolic blood pressure of the study patients measured at the beginning of the study, after 60 days ("2M"), and at the end of the study after 90 days ("3M"), shown in mmHg.

The average blood pressure of the patents at the beginning of the study, after two months, and after three months is shown in FIG. 7. The patients' blood pressure was stable during the course of the study.

These results show that the tested product resulted in a significant decrease in serum creatinine and increased glomerular filtration in patients with CKD. Small decreases in uric acid and cholesterol levels, and small increases in hemoglobin and serum iron, were also observed. These small changes were not statistically significant, but indicate a stabilization of the condition of the patients. No side effects were reported by the patients or detected in the medical monitoring tests. The tested product has therefore been shown to be safe and effective, having a positive effect on patents with CKD and slowing down CKD progression.

The various embodiments described above can be combined to provide further embodiments. All of the U.S. patents, U.S. patent application publications, U.S. patent applications, foreign patents, foreign patent applications and non-patent publications referred to in the specification and/or listed in the Application Data Sheet, including, but not limited to, U.S. Provisional Patent Application No. 62/638,692 filed Mar. 5, 2018, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A composition for regulation of kidney and excretory function in one of a tablet or capsule dosage form for oral delivery comprising active components consisting of:
   (i) about 30% to about 60% roundhead *Lespedeza* extract from aerial parts of the plant comprising lespedine and lespecapitoside;
   (ii) about 30% to about 60% birch leaf extract;
   (iii) about 5% to about 30% red bilberry extract; (iv) about 0.005% to about 3% vitamin B6; (v) about 0.005% to about 8% vitamin E; and
   (vi) about 0.005% to about 6% iron consisting of iron in a ferrous form.

2. The composition of claim 1, wherein the composition further comprises excipients in an amount that accounts for about 20% to 40% of the total weight (w/w) of the composition.

3. The composition of claim 1, wherein the composition includes the following amounts by weight of active components: about 4 mg vitamin $B_6$; about 9 mg vitamin E; about 6 mg iron; about 280 mg roundhead *Lespedeza* extract; about 250 mg birch leaf extract; and about 100 mg red bilberry extract.

4. The composition of claim 1, wherein the composition includes the following amounts by weight of active components: about 4 mg vitamin $B_6$; about 9 mg vitamin E; about 6 mg iron; about 250 mg roundhead *Lespedeza* extract; about 250 mg birch leaf extract; and about 100 mg red bilberry extract.

5. The composition of claim 1, wherein the composition further comprises one or more excipients selected from the group comprising: microcrystalline cellulose, polyvinylpyrrolidone, magnesium stearate, talc, and film coating.

6. The composition of claim 1, wherein the composition further comprises microcrystalline cellulose in the amount by weight of about 151 mg, polyvinylpyrrolidone in the amount of about 35 mg, magnesium stearate in the amount of about 5 mg, talc in the amount of about 10 mg, and film coating in the amount of about 30 mg.

7. The composition of claim 1, wherein the composition further comprises microcrystalline cellulose in the amount by weight of about 121 mg, polyvinylpyrrolidone in the amount of about 35 mg, magnesium stearate in the amount of about 5 mg, talc in the amount of about 10 mg, and film coating in the amount of about 30 mg.

8. The composition of claim 1, wherein the composition is a tablet and is, optionally, film coated or immediate release.

9. The composition of claim 3, wherein the composition comprises one or more dosage forms to deliver the active components.

10. The composition of claim 1, wherein said composition is a dosage form consisting of about 619 mg of active components and about 231 mg of excipients, and wherein the ratio by weight (w/w) of total dosage form weight for the active agents is about 0.5% vitamin B6, about 1.1% vitamin E, about 0.7% iron, about 29% dry extract of roundhead *Lespedeza*, about 29% dry extract of birch leaf, and about 12% dry extract of red bilberry, with the remaining about 231 mg of excipients comprising about 27% or about one-fourth to about one third of the total dosage form weight.

11. The composition of claim 1, wherein said composition is a dosage form consisting of about 649 mg of active components and may comprise an additional about 201 mg of excipients, and wherein the ratio by weight (w/w) of total dosage form weight for the active agents is about 0.5% vitamin B6, about 1.1% vitamin E, about 0.7% iron, about 34% dry extract of roundhead *Lespedeza*, about 29% dry extract of birch leaf, and about 12% dry extract of red bilberry, with the remaining about 201 mg of excipients comprising about 24% or about one-fifth to about one-third of the total dosage form weight.

12. The composition of claim 11, wherein the excipients consist of microcrystalline cellulose in an amount of about 121 mg, polyvinylpyrrolidone in an amount of about 35 mg, magnesium stearate in an amount of about 5 mg, talc in an amount of about 10 mg, and film coating in an amount of about 30 mg.

13. A method for regulating kidney and excretory system function, comprising administering a dosage form of claim 1.

\* \* \* \* \*